(12) United States Patent
Nishida et al.

(10) Patent No.: US 11,925,444 B2
(45) Date of Patent: Mar. 12, 2024

(54) BLOOD PRESSURE MEASUREMENT DEVICE

(71) Applicants: OMRON CORPORATION, Kyoto (JP); OMRON HEALTHCARE CO., LTD., Muko (JP)

(72) Inventors: Tomoyuki Nishida, Kyoto (JP); Takanori Nishioka, Kyoto (JP); Yoshihiko Sano, Kyoto (JP); Brian Brigham, Kyoto (JP); Takashi Ono, Kyoto (JP)

(73) Assignees: OMRON CORPORATION, Kyoto (JP); OMRON HEALTHCARE CO., LTD., Muko (JP)

( * ) Notice: Subject to any disclaimer, the term of this patent is extended or adjusted under 35 U.S.C. 154(b) by 638 days.

(21) Appl. No.: 16/912,742

(22) Filed: Jun. 26, 2020

(65) Prior Publication Data

US 2020/0323445 A1     Oct. 15, 2020

Related U.S. Application Data

(63) Continuation of application No. PCT/JP2018/043760, filed on Nov. 28, 2018.

(30) Foreign Application Priority Data

Dec. 28, 2017  (JP) .................................. 2017-252905

(51) Int. Cl.
*A61B 5/022*  (2006.01)
*A61B 5/00*   (2006.01)
(Continued)

(52) U.S. Cl.
CPC ........ *A61B 5/02233* (2013.01); *A61B 5/0235* (2013.01); *A61B 5/681* (2013.01); *A61B 2562/0219* (2013.01)

(58) Field of Classification Search
CPC ... A61B 5/02233; A61B 5/0235; A61B 5/681; A61B 2562/0219; A61B 5/0225; A61B 5/02141
See application file for complete search history.

(56) References Cited

U.S. PATENT DOCUMENTS

| | | | | |
|---|---|---|---|---|
| 4,860,761 A | * | 8/1989 | Yamasawa | A61B 5/02255 600/499 |
| 6,336,901 B1 | * | 1/2002 | Itonaga | A61B 5/681 600/499 |

(Continued)

FOREIGN PATENT DOCUMENTS

| | | | |
|---|---|---|---|
| JP | 05269089 A | * | 10/1993 |
| JP | 2007-175185 A | | 7/2007 |

(Continued)

OTHER PUBLICATIONS

Machine translation of JP05269089A (Year: 1993).*
Feb. 12, 2019 International Search Report issued in International Patent Application No. PCT/JP2018/043760.

*Primary Examiner* — Alex M Valvis
*Assistant Examiner* — Justin Xu
(74) *Attorney, Agent, or Firm* — Oliff PLC

(57) ABSTRACT

A blood pressure measurement device includes a bag-like pressing cuff wound around a measurement target site of a living body; a back plate arranged on the living body side of the pressing cuff; a bag-like sensing cuff arranged on the living body side of the back plate; a supply device configured to supply a fluid into the cuffs; first guides arranged on the living body side of the pressing cuff and configured to form wrinkles in a direction intersecting the winding direction; and second guides arranged on the living body side of the sensing cuff and configured to form wrinkles in the direction intersecting the winding direction.

7 Claims, 19 Drawing Sheets

(51) Int. Cl.
  *A61B 5/021*    (2006.01)
  *A61B 5/0235*   (2006.01)
  *A61B 5/0225*   (2006.01)

(56) References Cited

U.S. PATENT DOCUMENTS

| | | | | |
|---|---|---|---|---|
| 2009/0062668 | A1* | 3/2009 | Todokoro | A61B 5/02233 |
| | | | | 600/499 |
| 2009/0163823 | A1* | 6/2009 | Takahashi | A61B 5/6843 |
| | | | | 600/490 |
| 2011/0112412 | A1* | 5/2011 | Sano | A61B 5/02233 |
| | | | | 600/499 |
| 2011/0251498 | A1* | 10/2011 | Nasella | A61B 5/022 |
| | | | | 600/490 |
| 2012/0150051 | A1* | 6/2012 | Kinsley | A61B 5/02233 |
| | | | | 600/499 |
| 2013/0060153 | A1 | 3/2013 | Kobayashi et al. | |
| 2014/0187987 | A1 | 7/2014 | Fraden et al. | |
| 2015/0359446 | A1 | 12/2015 | Pfeiffer et al. | |

FOREIGN PATENT DOCUMENTS

| | | |
|---|---|---|
| JP | 2016-509516 A | 3/2016 |
| WO | 2011/122103 A1 | 10/2011 |
| WO | 2014/102870 A1 | 7/2014 |
| WO | 2014/102871 A1 | 7/2014 |

\* cited by examiner

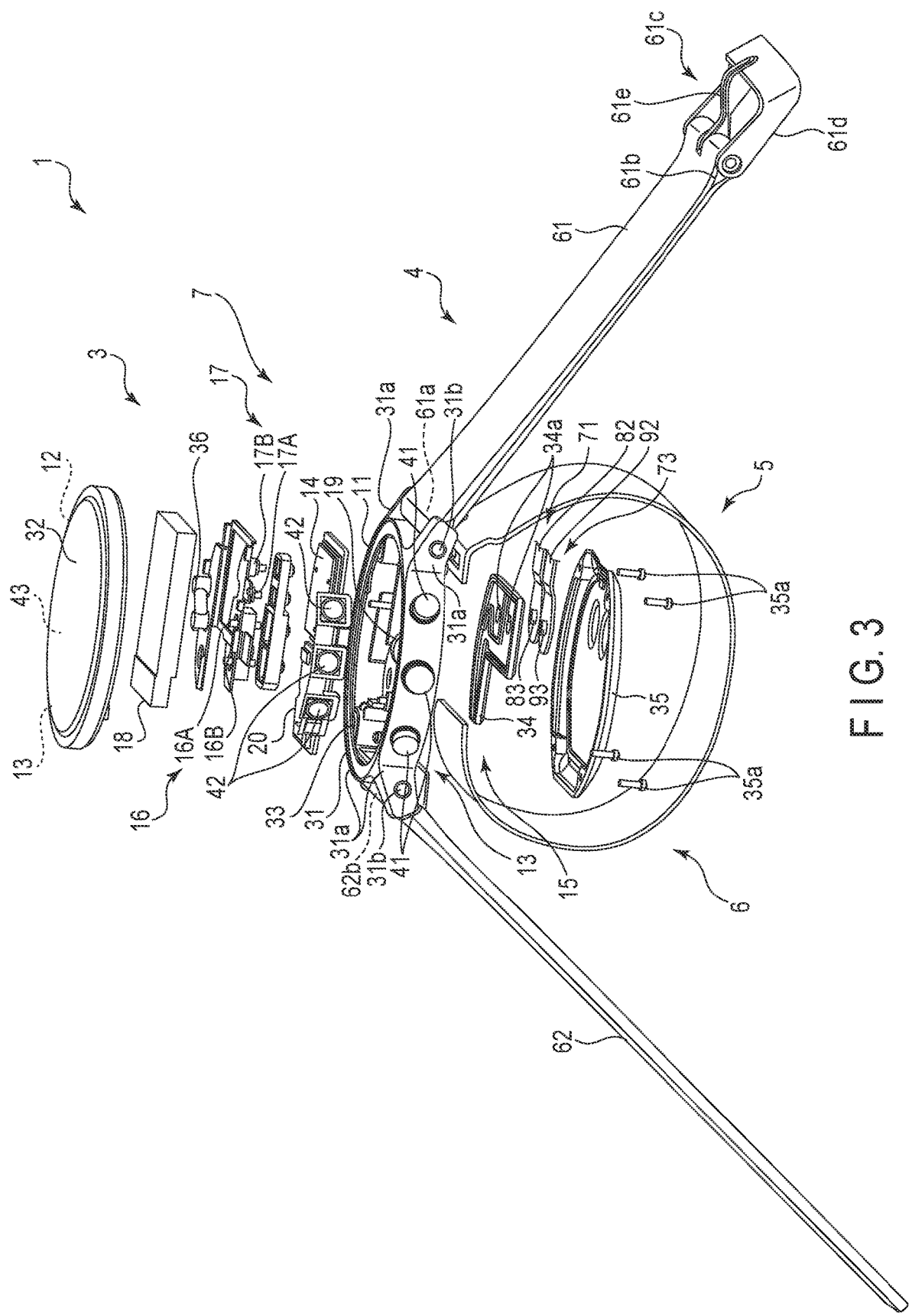
F I G. 3

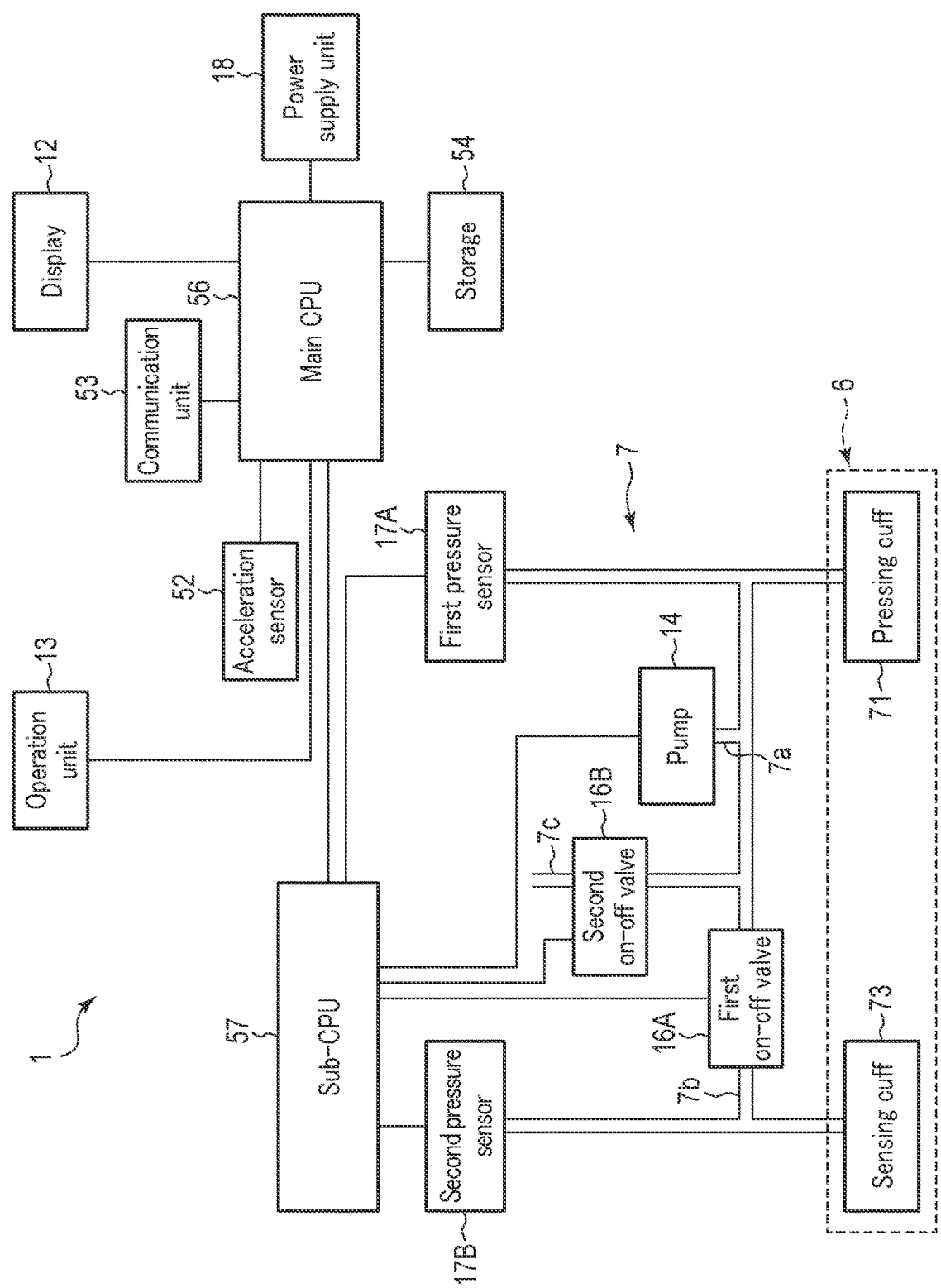
F I G. 4

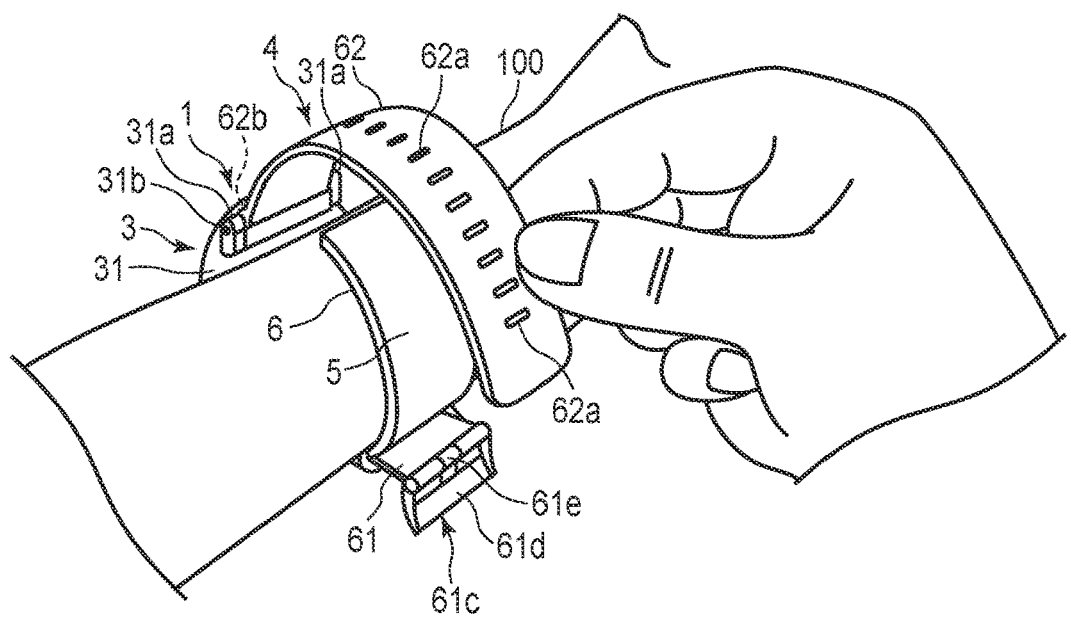
F I G. 16
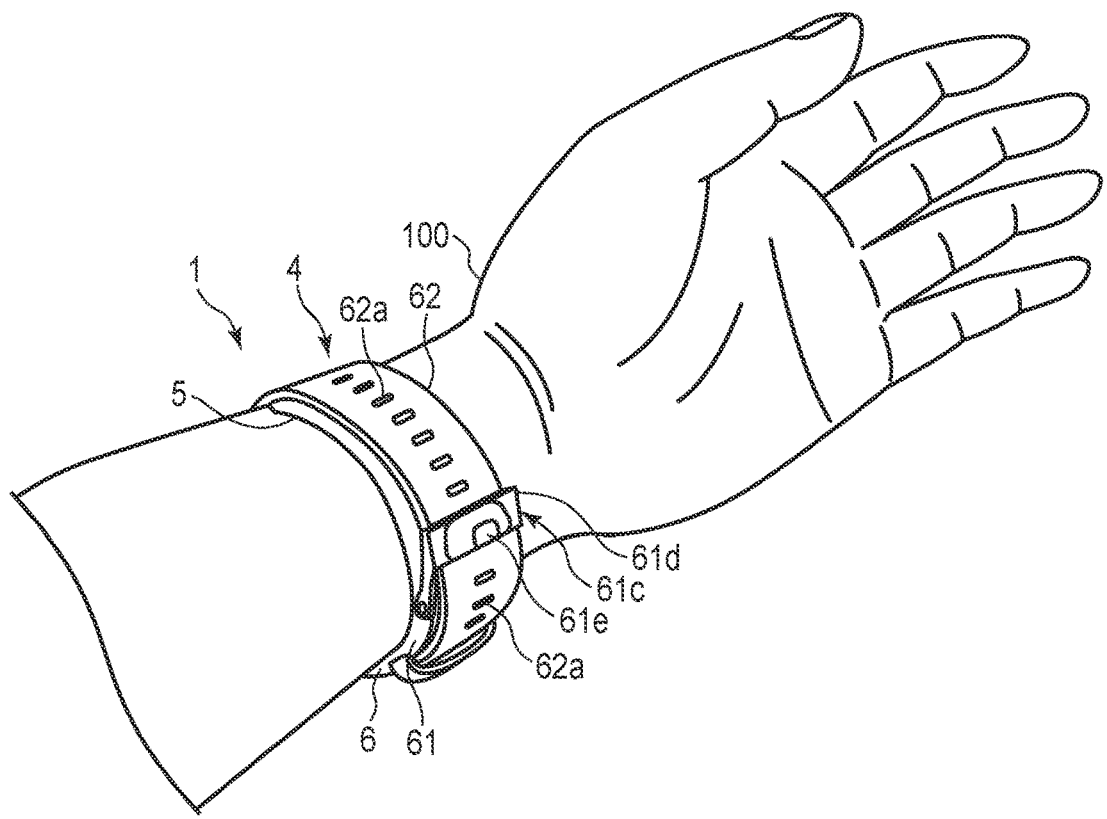
F I G. 17

F.I.G. 19

BLOOD PRESSURE MEASUREMENT DEVICE

CROSS-REFERENCE TO RELATED APPLICATIONS

This is a Continuation Application of PCT application No. PCT/JP2018/043760, filed Nov. 28, 2018, which was published under PCT Article 21(2) in Japanese.

This application is based upon and claims the benefit of priority from Japanese Patent Application No. 2017-252905, filed Dec. 28, 2017, the entire contents of which are incorporated herein by reference.

BACKGROUND

Field

The present invention relates to a blood pressure measurement device for the measurement of blood pressure.

Description of the Related Art

Recently, blood pressure measurement device have been employed not only in medical facilities but also at home as a means for checking health conditions. Blood pressure may be measured by winding a cuff of a blood pressure measurement device around an upper arm or wrist of a living body, inflating and contracting the cuff, detecting the pressure of the cuff with the pressure sensor, and thereby detecting the vibration of the artery wall.

When the cuff is wound around the living body and inflated, a difference appears between the lengths of the outer peripheral surface and inner peripheral surface of the inflated cuff, wrinkling the living-body side of the cuff. The wrinkles in the cuff may vary in their number, positions and depths, depending on the circumference and shape of the living body around which the cuff is wound, the winding manner of the cuff, and the like.

Depending on the number, positions and depths of the wrinkles in the cuff, a division inside the cuff may be created, or a loss of inflating pressure may occur. This may adversely affect the measurement result of the blood pressure such as decreasing the accuracy of the blood pressure measurement and causing variations in the measurement result.

A cuff for a blood pressure measurement device capable of suppressing wrinkling in a bag-like cover has been known, as disclosed in Jpn. Pat. Appln. KOKAI Publication No. 2007-175185. In such a blood pressure measurement device cuff, a curler is included in the bag-like cover that contains an air bag, and this curler has a large curvature portion and a small curvature portion in the winding direction so that the cuff can fit the measurement target site. When the air bag is in an uninflated state, a portion of an inner cover component corresponding to the large curvature portion of the curler is stretched in the width direction so that wrinkling can be suppressed. This blood pressure measurement device cuff may demonstrate such an effect through a configuration in which the widths of the inner cover component and outer cover component seamed together in the portion of the bag-like cover corresponding to the large curvature portion of the curler differ from the seamed widths in other portions.

SUMMARY

In general, in addition to the above-mentioned configuration of the blood pressure measurement device cuff having an air bag and a curler in a bag-like cover, a configuration of a cuff to which a fluid is supplied and which is brought into contact with the living body, and a configuration in which a plurality of air bags are stacked have also been known. For such cuffs of various types, a technique for suppression of wrinkles adversely affecting the measurement result of the blood pressure, is demanded.

According to one aspect of the invention, a blood pressure measurement device can be provided, which includes a bag-like pressing cuff configured to be wound around a measurement target site of a living body and inflated with a fluid supplied to the internal space thereof; a bag-like sensing cuff arranged on the living body side of the pressing cuff, arranged, when the pressing cuff is wound around the living body, in the area of the measurement target site where the artery runs, and inflated with a fluid supplied to the internal space thereof; a supply device configured to supply the fluid into the pressing cuff and the sensing cuff; first guides arranged on the living body side of the pressing cuff and configured to form wrinkles on the living body side of the pressing cuff, in a direction intersecting the winding direction of the pressing cuff, when the pressing cuff is inflated to pressurize the living body; and second guides arranged on the living body side of the sensing cuff and configured to form wrinkles on the living body side of the sensing cuff, in a direction intersecting the winding direction of the pressing cuff, when the sensing cuff is inflated to pressurize the living body.

Here, the fluid may include liquid and air. Wrinkles are creases that are created in the inner peripheral surface of the pressing cuff or sensing cuff when the bag-like pressing cuff or sensing cuff wound around the living body is inflated and a difference appears between the lengths of the outer peripheral surface and inner peripheral surface of the pressing cuff or sensing cuff (inner/outer peripheral difference), part of the inner peripheral surface thereby moving toward the outer peripheral surface side. The measurement target site is an area of the living body where the artery runs and the blood pressure can be measured. This may be the wrist, upper arm or ankle.

The pressing cuff and sensing cuff are bag-like structures, such as air bags, that are inflated when wound around the measurement target site of the living body such as the wrist to measure the blood pressure and the fluid is supplied thereto. Here, the supply device is a main body of the blood pressure measurement device including a pump and a flow passage.

According to this aspect of the invention, when the pressing cuff and sensing cuff are wound and inflated around the living body, wrinkles that appear on the inner peripheral surface side due to the inner/outer peripheral difference are formed by the guides, as a result of which the positions and depths of the wrinkles become controllable.

The wrinkles formed in the inner peripheral surface of the pressing cuff or sensing cuff may divide the internal space of the pressing cuff or sensing cuff, or, depending on their positions and depths, may produce variation in the pressure of the cuff pressurizing the living body. This may decrease the accuracy of the measured blood pressure values or incur other adverse effects on the measurement result of the blood pressure. With the arrangement of the guides, however, the positions of the wrinkles that appear in the inner peripheral surface of the pressing cuff or sensing cuff can be controlled. This can suppress the variation incurred by the difference in the individual living bodies, the conditions of the use of the cuffs and the like, in the positions and depths of the wrinkles that appear in the inner peripheral surfaces of the pressing cuff and sensing cuff when the pressing cuff and sensing cuff are inflated. In this manner, the blood pressure measurement device can reliably pressurize the living body with the pressing cuff or sensing cuff, thus preventing the measured blood pressure values from varying, and can also improve the accuracy of the measurement result of the blood pressure.

In the aforementioned aspect of the invention, a blood pressure measurement device can be offered, in which the first guides are a plurality of grooves in the outer surface of the pressing cuff on the living body side, and the second guides are a plurality of grooves in the outer surface of the sensing cuff on the living body side.

According to this aspect of the invention, with the first guides and second guides, which are formed as grooves, the control of wrinkles can be achieved by a simple structure, without increasing the thickness of the cuffs.

In the aforementioned aspect of the invention, a blood pressure measurement device can be provided, in which the plurality of first guides and the plurality of second guides are arranged at regular intervals.

According to this aspect of the invention, wrinkles are formed at regular intervals in the inner peripheral surfaces of the pressing cuff and sensing cuff, thereby making the depths of the wrinkles uniform. This prevents some of the wrinkles from having a greater depth than others.

In the aforementioned aspect of the invention, a blood pressure measurement device can be provided, in which the plurality of second guides are arranged at the same positions with respect to the winding direction of the pressing cuff as the first guides arranged in an area of the pressing cuff facing the sensing cuff.

According to this aspect of the invention, the second guides are provided at the same positions as some of the first guides. Thus, the pressing cuff can pressurize, at its unwrinkled portion, an unwrinkled portion of the sensing cuff. This allows the sensing cuff to desirably pressurize the measurement target site.

In the aforementioned aspect of the invention, a blood pressure measurement device can be provided, which includes a back plate arranged on the living body side of the pressing cuff, having the sensing cuff on the living body side, and extending in the circumferential direction of the measurement target site of the living body.

According to this aspect of the invention, with the back plate arranged between the pressing cuff and the sensing cuff, the pressing force of the pressing cuff is conducted to the sensing cuff by way of the back plate, and the sensing cuff can thereby be uniformly pressurized.

In the aforementioned aspect of the invention, a blood pressure measurement device can be provided, in which the first guides and the second guides form wrinkles in a direction perpendicular to the winding direction of the pressing cuff.

According to this aspect of the invention, with the wrinkles created in the direction perpendicular to the winding direction of the cuff around the living body, the wrinkles in the cuff would not overlap with one another.

The present invention offers a blood pressure measurement device that can improve the accuracy of the measurement result of the blood pressure by suppressing the appearance of wrinkles.

BRIEF DESCRIPTION OF THE DRAWINGS

FIG. 3 is an exploded view showing the configuration of the blood pressure measurement device.

FIG. 4 is a block diagram showing the configuration of the blood pressure measurement device.

FIG. 16 is a perspective view showing an example of the blood pressure measurement device being attached around the wrist.

FIG. 17 is a perspective view showing an example of the blood pressure measurement device being attached around the wrist.

DETAILED DESCRIPTION

First Embodiment

An example of a blood pressure measurement device 1 according to the first embodiment of the present invention will be described with reference to FIGS. 1 to 13.

Figure 1:
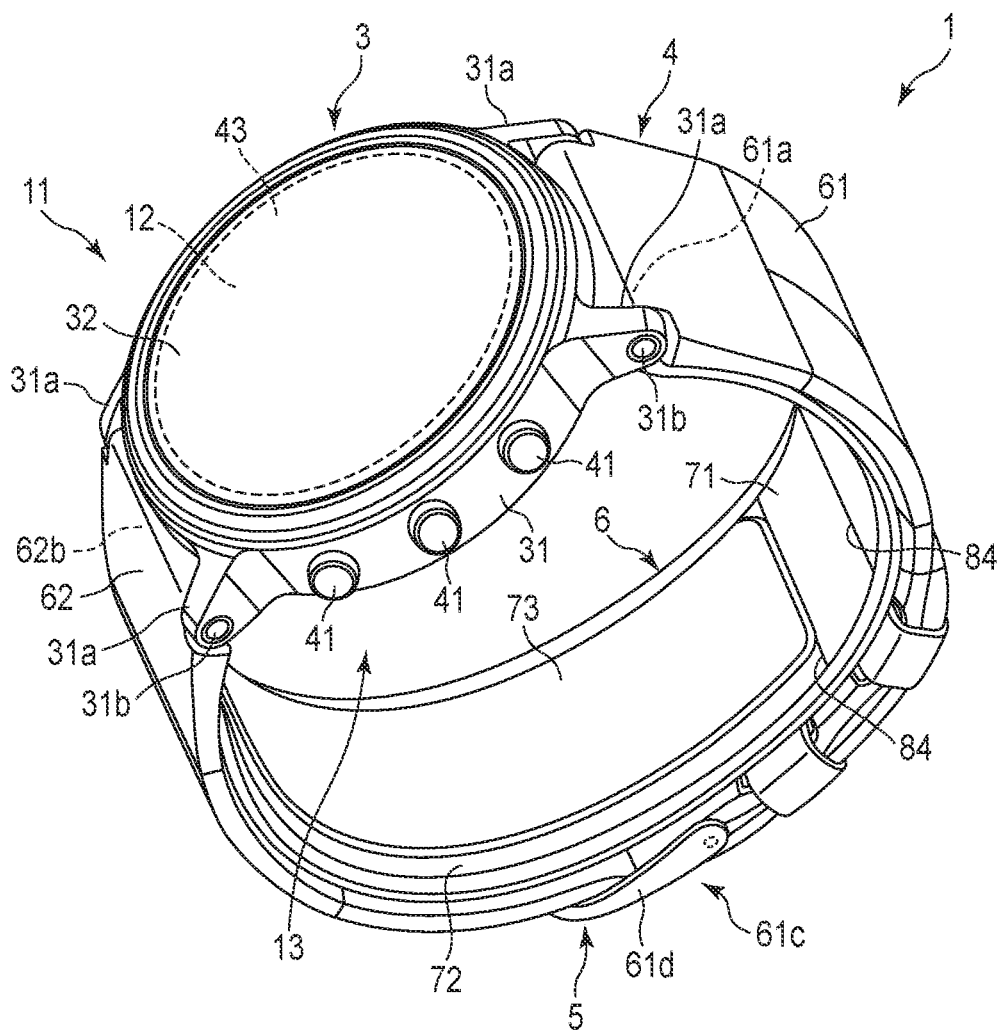
FIG. 1 is a perspective view showing the configuration of a blood pressure measurement device according to the first embodiment of the present invention.
Figure 2:
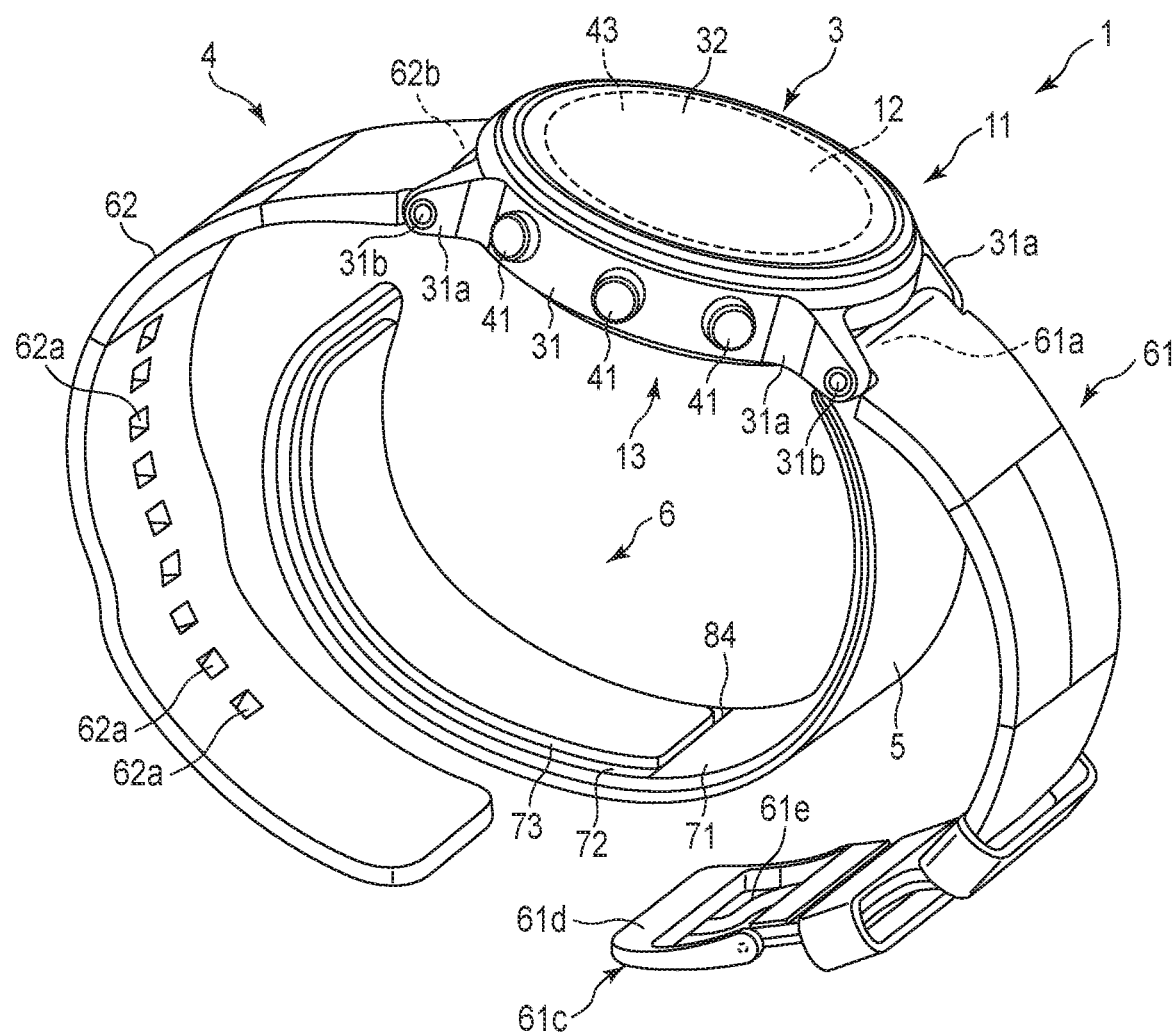
FIG. 2 is a perspective view showing the configuration of the blood pressure measurement device.
Figure 5:
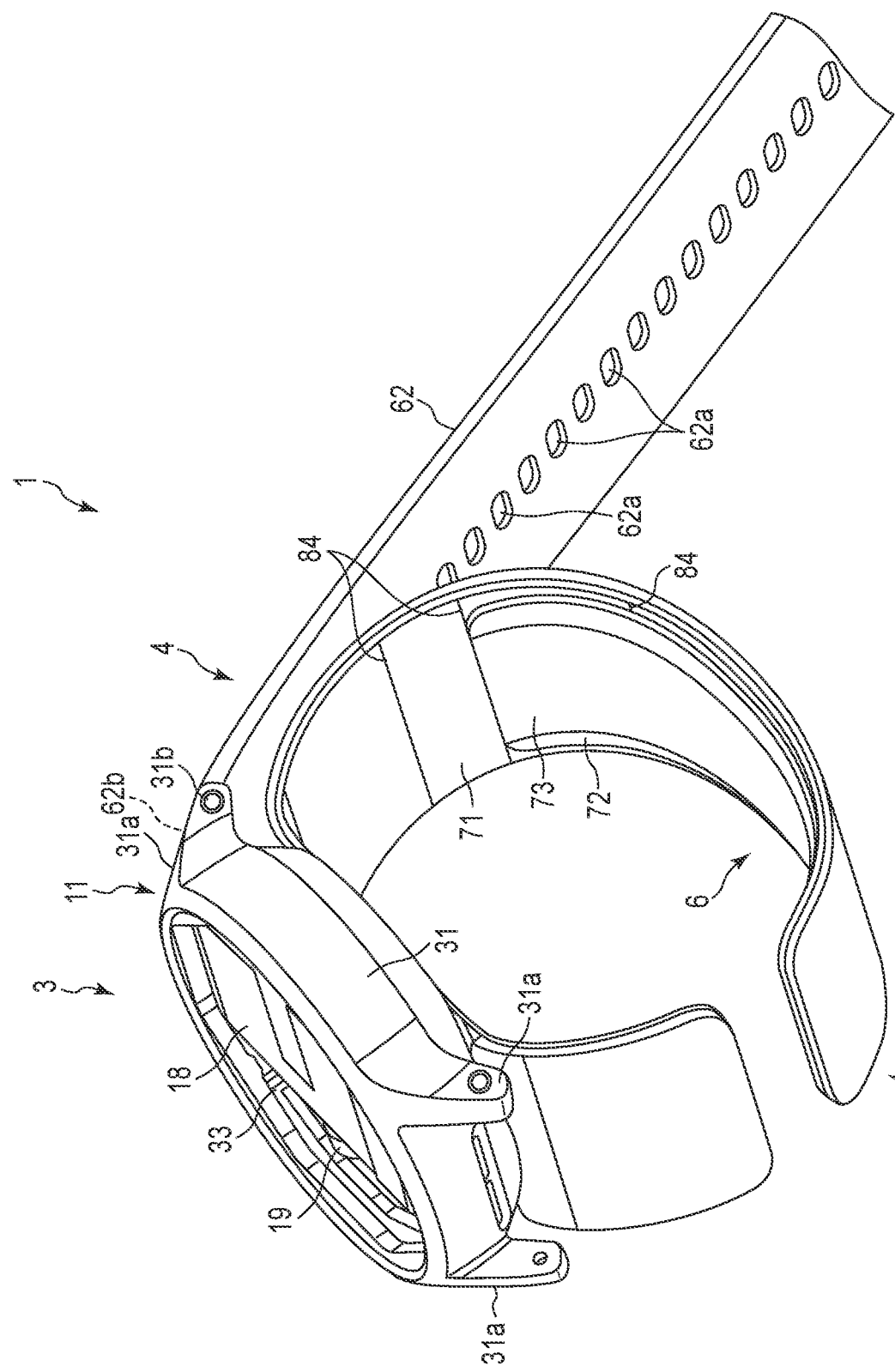
FIG. 5 is a perspective view showing another configuration of the blood pressure measurement device.
Figure 6:
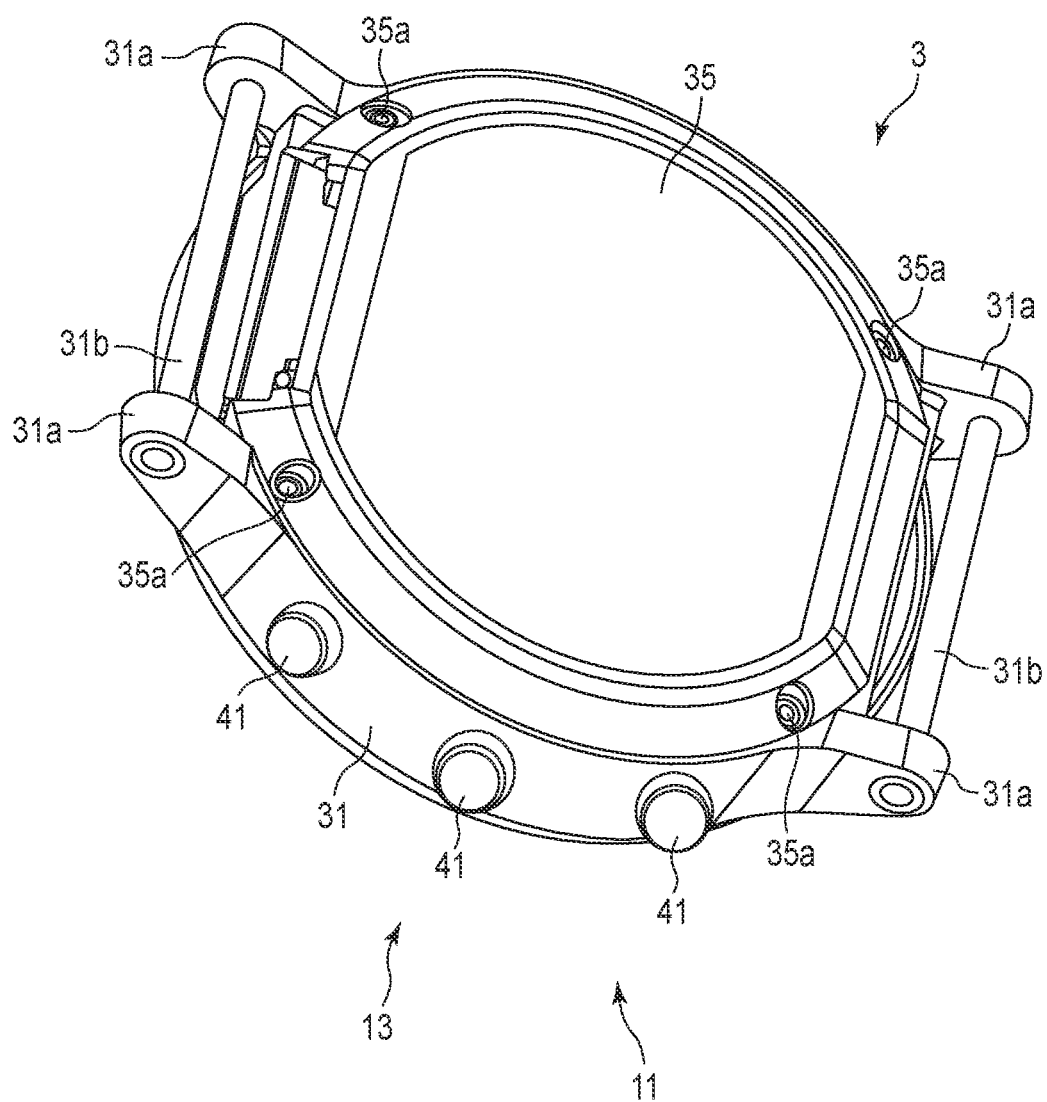
FIG. 6 is a perspective view showing the configuration of the main body of the blood pressure measurement device.
Figure 7:
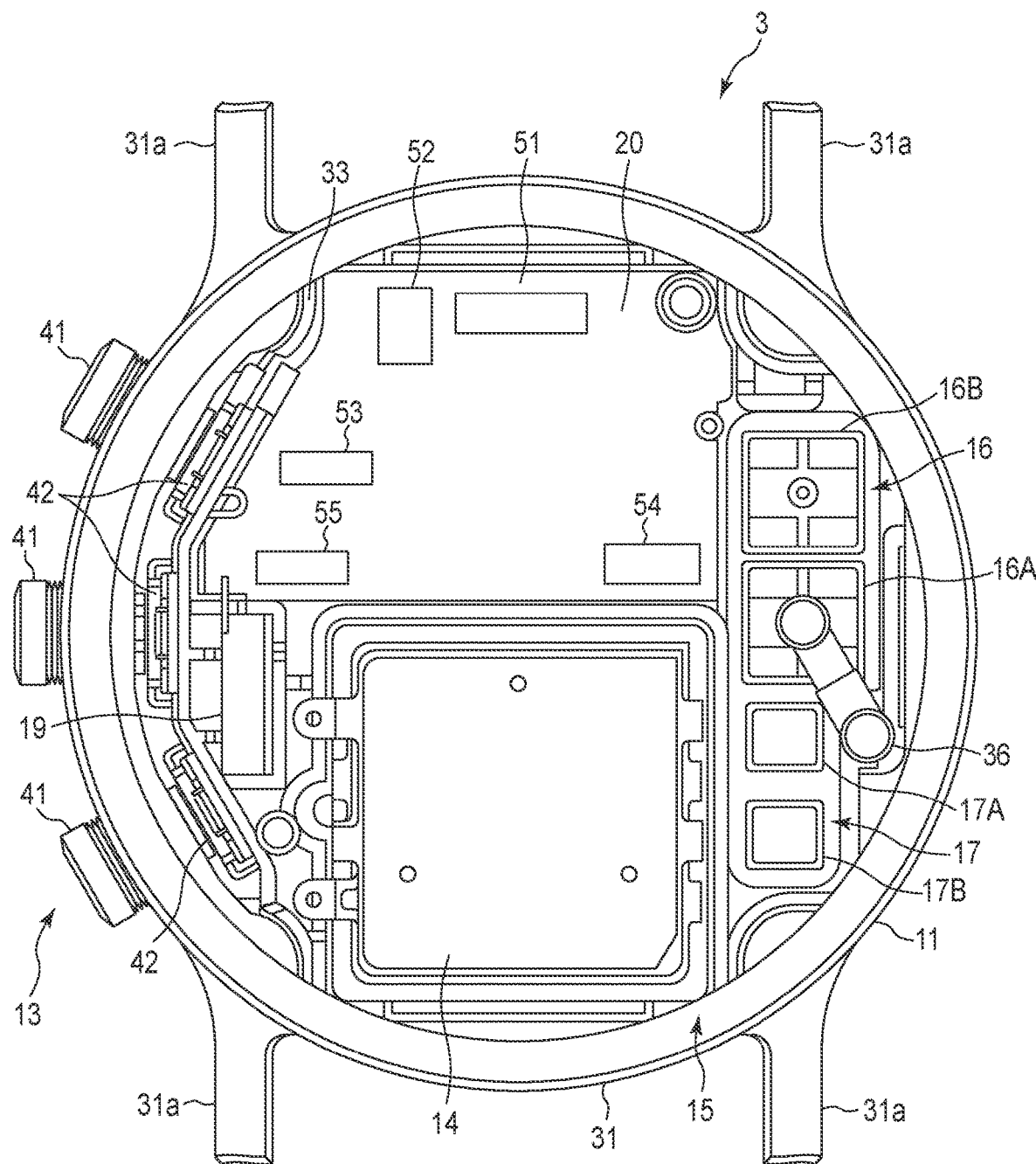
FIG. 7 is a plan view showing the internal configuration of the main body.
Figure 8:
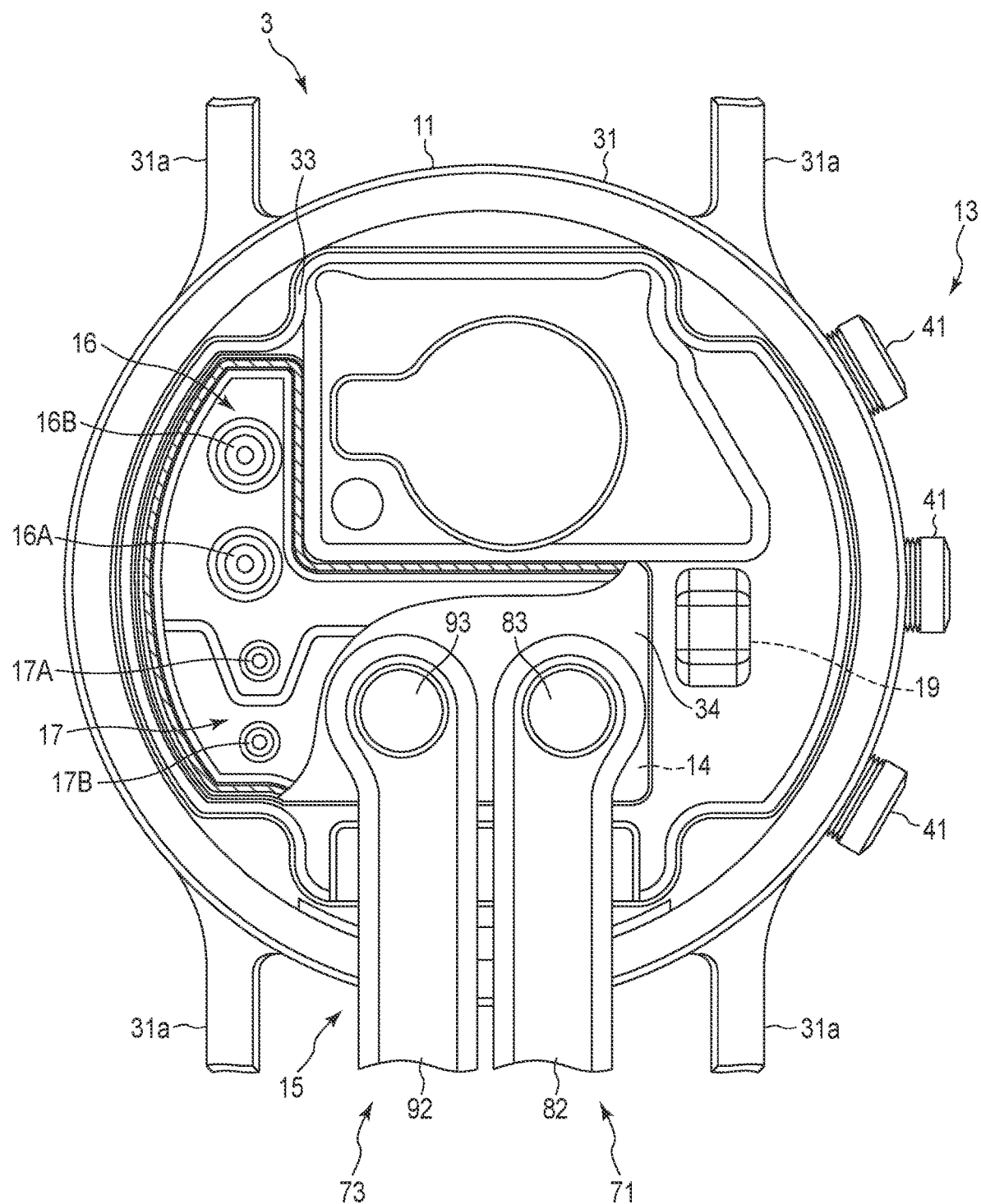
FIG. 8 is a plan view showing the internal configuration of the main body.
Figure 9:
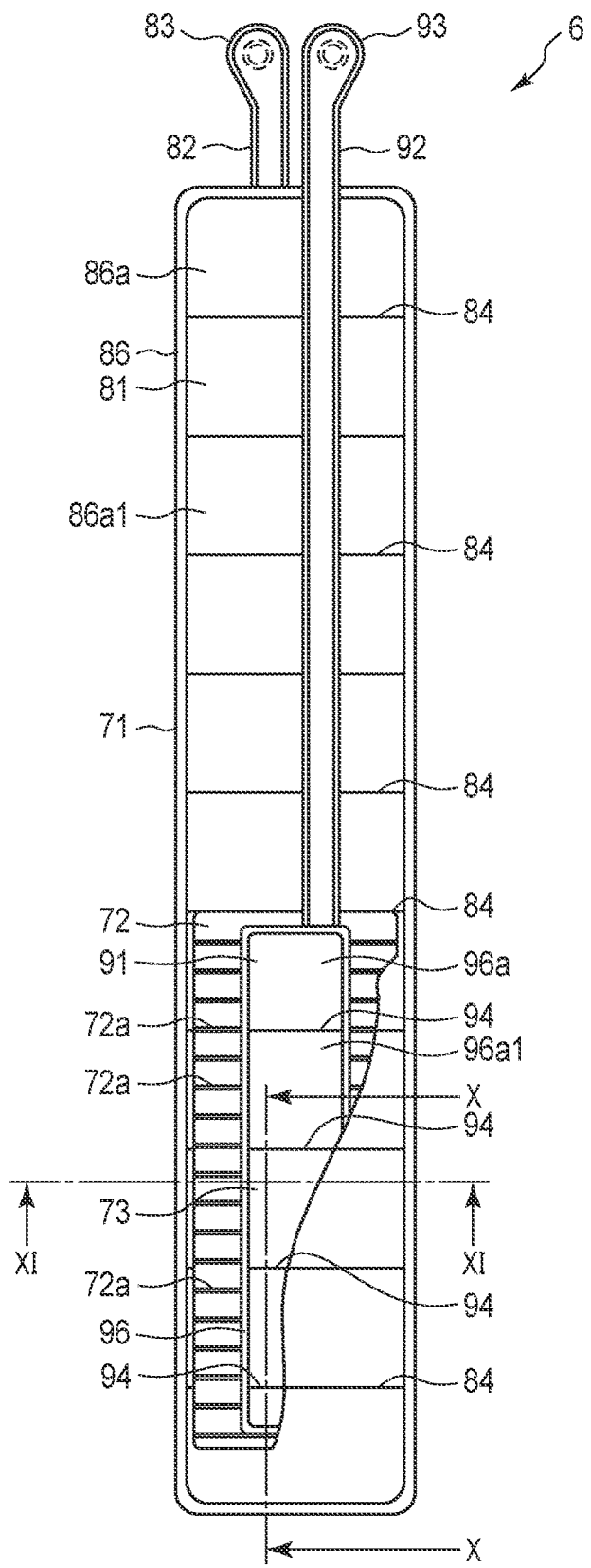
FIG. 9 is a plan view showing the configuration of the cuff structure of the blood pressure measurement device.

FIG. 1 is a perspective view of the configuration of the blood pressure measurement device 1 according to the first embodiment of the present invention with a strap 4 buckled. FIG. 2 is a perspective view of the configuration of the blood pressure measurement device 1 with the strap 4 unbuckled. FIG. 3 is an exploded view of the configuration of the blood pressure measurement device 1. FIG. 4 is a block diagram of the configuration of the blood pressure measurement device 1. FIG. 5 is a perspective view of another configuration of the blood pressure measurement device 1. FIG. 6 is a perspective view of the configuration of the main body 3 of the blood pressure measurement device 1 when viewed from the back cover 35 side. FIGS. 7 and 8 are plan views of the internal configuration of the main body 3 when viewed from the windshield 32 side and the back cover 35 side, respectively. FIG. 9 is a plan view of the configuration of the cuff structure 6 of the blood pressure measurement device 1 when viewed from the sensing cuff 73 side.

Figure 10:
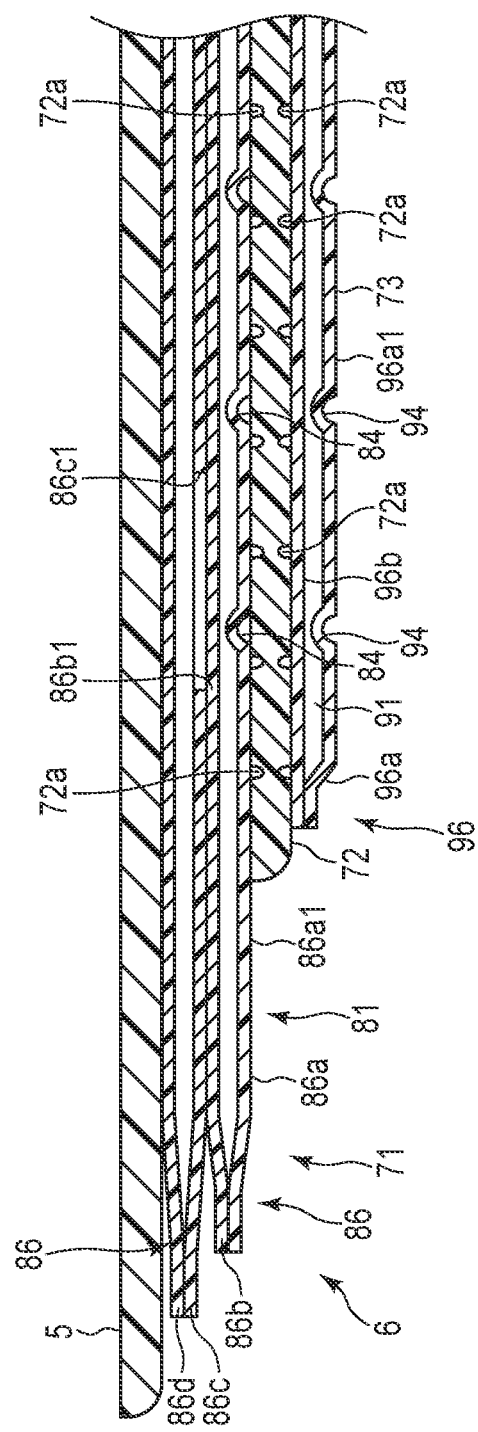
FIG. 10 is a cross-sectional view showing the configuration of the curler and cuff structure of the blood pressure measurement device.
Figure 11:
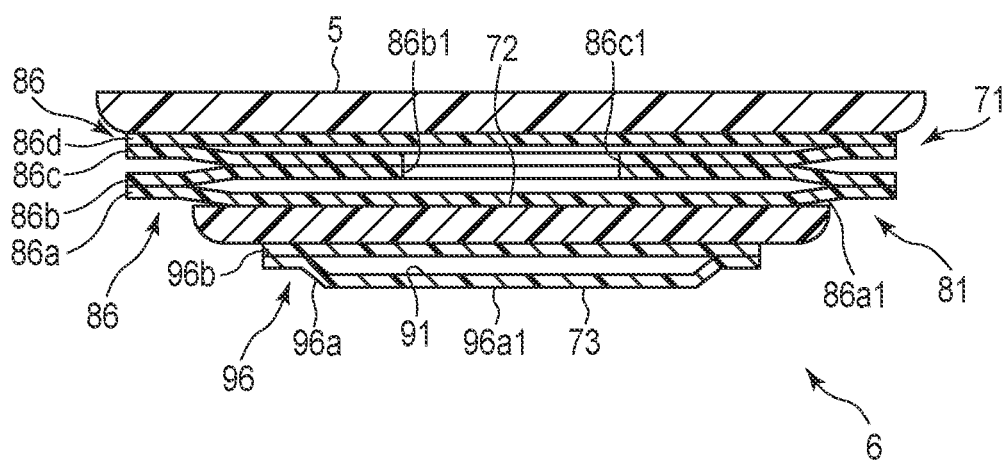
FIG. 11 is a cross-sectional view of the configuration of the curler and cuff structure.
Figure 12:
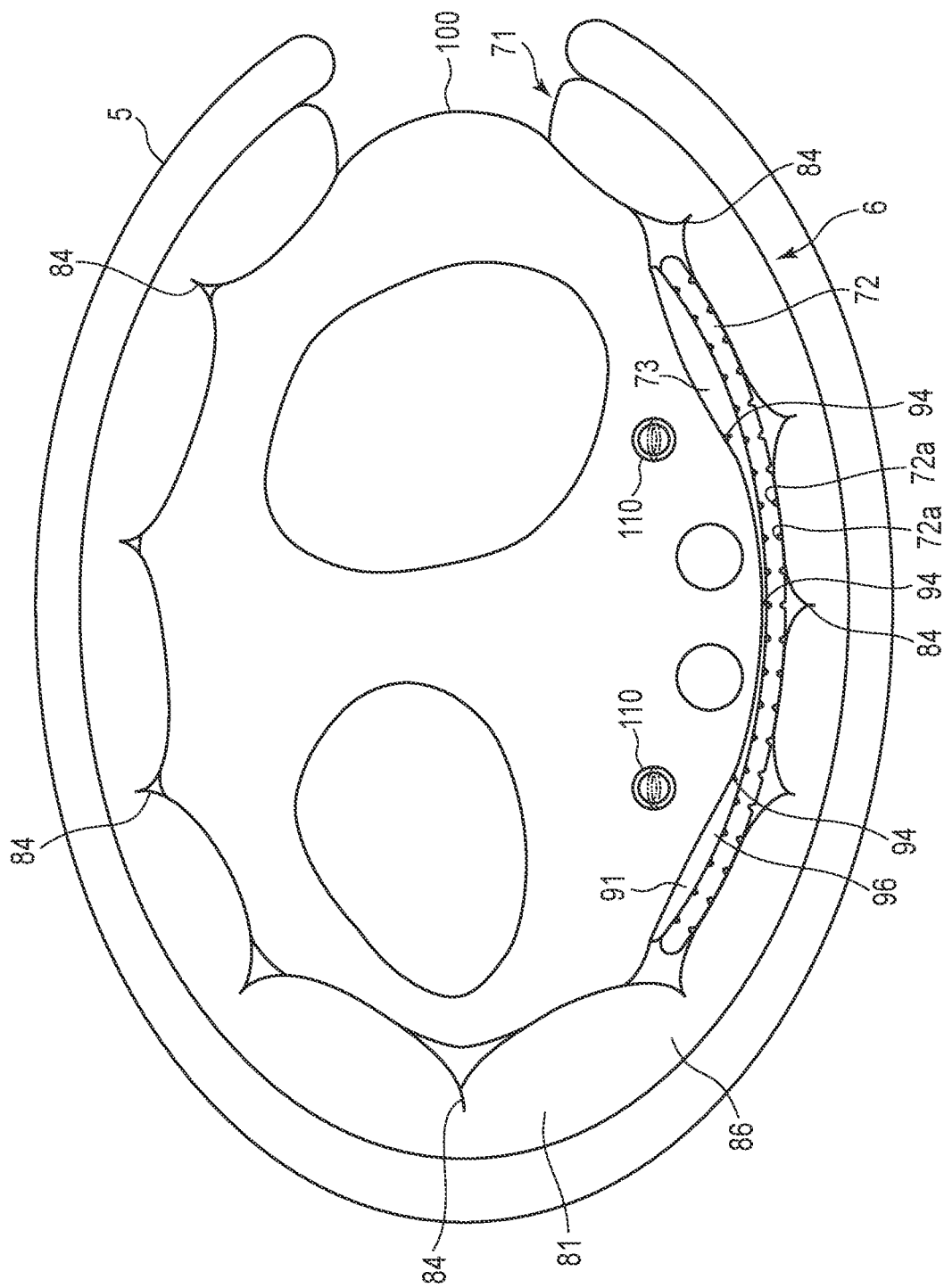
FIG. 12 is a side view schematically showing the configuration of the pressing cuff of the cuff structure when inflated.
Figure 13:
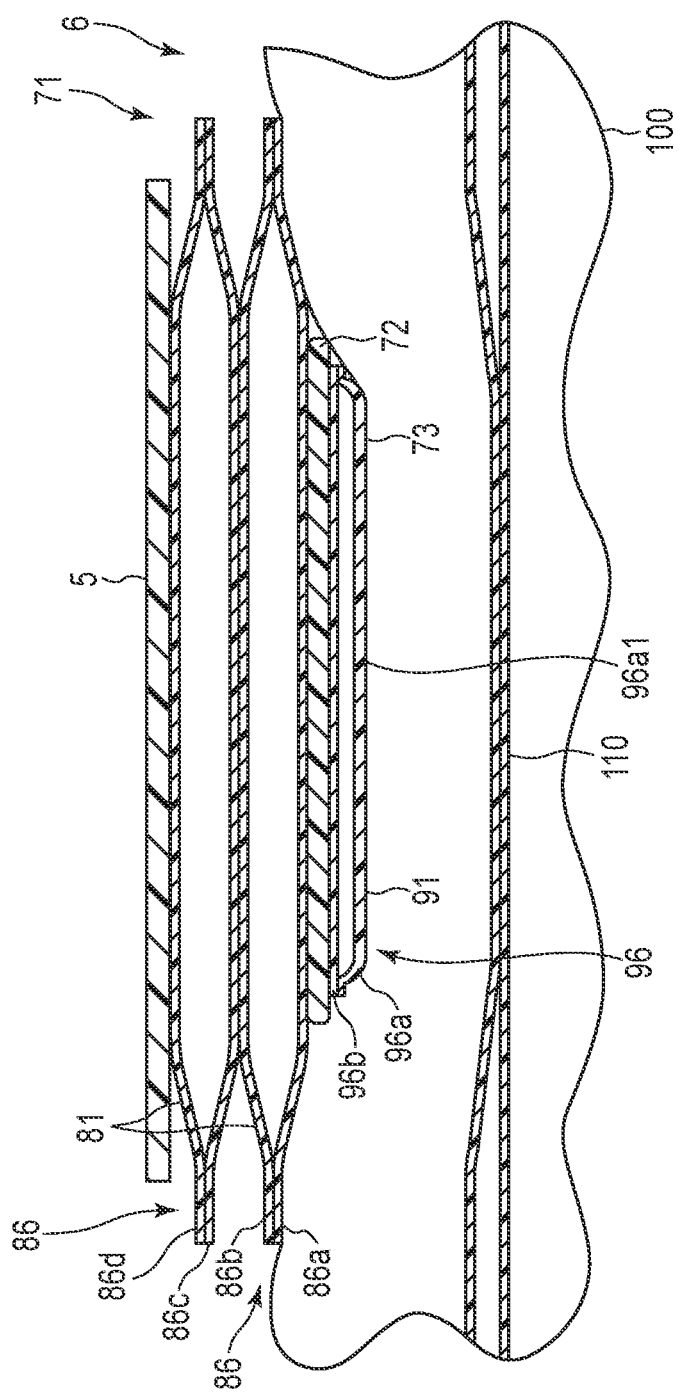
FIG. 13 is a cross-sectional view schematically showing the configuration of the pressing cuff of the cuff structure when inflated.

FIG. 10 is a cross-sectional view schematically showing the configuration of the curler 5 and cuff structure 6 of the blood pressure measurement device 1 along the line X-X in FIG. 9. FIG. 11 is a cross-sectional view of the configuration of the curler 5 and the cuff structure 6 along the line XI-XI in FIG. 9. FIGS. 12 and 13 are a side view and cross-sectional view schematically illustrating the pressing cuff 71 and sensing cuff 73 of the cuff structure 6 when inflated. In FIG. 10, the curler 5 and cuff structure 6 are linearly illustrated for the simplicity of explanation; however, in the actual arrangement in the blood pressure measurement device 1, they have a bent form.

The blood pressure measurement device 1 is an electronic blood pressure measurement device configured to be attached to a living body. The explanation of the blood pressure measurement device 1 according to the present embodiment will be given using an electronic blood pressure measurement device configured to be attached to the wrist 100 of the living body. The blood pressure measurement device 1 may be an electronic blood pressure measurement device configured to be attached to the upper arm. As shown in FIGS. 1 to 12, the blood pressure measurement device 1 includes a main body 3, a strap 4, a curler 5, a cuff structure 6 including a pressing cuff 71 and a sensing cuff 73, and a fluid circuit 7.

As illustrated in FIGS. 1 to 8, the main body 3 includes a casing 11, a display 12, an operation unit 13, a pump 14, a flow passage unit 15, an on-off valve 16, a pressure sensor 17, a power supply unit 18, a vibration motor 19, and a control substrate 20. The main body 3 is a supply device that supplies fluid to the pressing cuff 71 with the pump 14, on-off valve 16, pressure sensor 17, control substrate 20 and the like.

The casing 11 includes an outer casing 31, a windshield 32 that covers the upper opening of the outer casing 31, a base 33 arranged inside the outer casing 31 at the bottom thereof, a flow passage cover 34 that covers part of the rear side of the base 33, and a back cover 35 that covers the bottom of the outer casing 31. The casing 11 further includes a flow passage tube 36 that constitutes part of the fluid circuit 7.

The outer casing 31 is cylindrically formed. The outer casing 31 includes a pair of lugs 31*a* arranged at each of symmetrical positions in the circumferential direction of the outer peripheral surface, and a spring rod 31*b* arranged between each pair of lugs 31*a*. The windshield 32 is a circular glass panel.

The base 33 holds the display 12, the operation unit 13, the pump 14, the on-off valve 16, the pressure sensor 17, the power supply unit 18, the vibration motor 19 and the control substrate 20. The base 33 also constitutes part of the flow passage unit 15.

The flow passage cover 34 is fixed to the rear surface of the base 33, or in other words the outer surface thereof, on the back cover 35 side. A groove is provided in either one of or both of the base 33 and flow passage cover 34, thereby constituting part of the flow passage unit 15.

The back cover 35 covers the end of the outer casing 31 on the living body side. The back cover 35 may be fixed by four screws 35*a* or the like to the end portion of the outer casing 31 or base 33 on the living body side.

The flow passage tube 36 constitutes part of the flow passage unit 15. The flow passage tube 36 may be coupled to the on-off valve 16 and the part of the base 33 that constitutes the flow passage unit 15.

The display 12 is arranged on the base 33 of the outer casing 31 and immediately below the windshield 32. The display 12 is electrically coupled to the control substrate 20. The display 12 may be a liquid crystal display or organic electroluminescence display. The display 12 displays various kinds of information that includes time/date and measurement results such as blood pressure values including the systolic blood pressure and diastolic blood pressure, and heart rates.

The operation unit 13 is designed in a manner such that an instruction from a user can be input. The operation unit 13 may include a plurality of buttons 41 arranged on the casing 11, a sensor 42 configured to detect the manipulation of the buttons 41, and a touch panel 43 arranged on the display 12 or windshield 32. The operation unit 13 converts an instruction to an electric signal through the manipulation of the user. The sensor 42 and touch panel 43 are electrically coupled to the control substrate 20 so that the electric signal can be output to the control substrate 20.

The buttons 41 may include three buttons. The buttons 41 are supported by the base 33, protruding from the outer peripheral surface of the outer casing 31. The buttons 41 and sensors 42 are supported by the base 33. The touch panel 43 may be arranged integrally with the windshield 32.

The pump 14 may be a piezoelectric pump. The pump 14 compresses the air, and supplies the compressed air to the cuff structure 6 by way of the flow passage unit 15. The pump 14 is electrically coupled to the controller 55.

The flow passage unit 15 is a passage of air formed by the groove or the like provided in the main surface of the base 33 on the back cover 35 side and the flow passage cover 34 that covers the back cover 35 side of the base 33. The flow passage unit 15 constitutes the passage extending from the pump 14 to the pressing cuff 71 and the passage extending from the pump 14 to the sensing cuff 73. Furthermore, the flow passage unit 15 constitutes a passage from the pressing cuff 71 to the ambient air and a passage from the sensing cuff 73 to the ambient air. The flow passage cover 34 includes a connected portion 34*a* to which the pressing cuff 71 and sensing cuff 73 are coupled. The connected portion 34*a* may be a cylindrical nozzle provided in the flow passage cover 34.

The on-off valve 16 opens and closes part of the flow passage unit 15. The on-off valve 16 may include a plurality of valves so that the flow passage from the pump 14 to the pressing cuff 71, the flow passage from the pump 14 to the sensing cuff 73, the flow passage from the pressing cuff 71 to the ambient air and the flow passage from the sensing cuff 73 to the ambient air can be selectively opened and closed through a combination of the opening and closing of the on-off valves 16. For example, two on-off valves 16 may be adopted.

The pressure sensor 17 detects the pressures of the pressing cuff 71 and the sensing cuff 73. The pressure sensor 17 is electrically coupled to the control substrate 20. The pressure sensor 17 is electrically coupled to the control substrate 20, converts the detected pressure to an electric signal, and outputs the signal to the control substrate 20. The pressure sensor 17 may be provided in the flow passage extending from the pump 14 to the pressing cuff 71 and the flow passage extending from the pump 14 to the sensing cuff 73. The pressures of these flow passages, which continue to the pressing cuff 71 and the sensing cuff 73, are the pressures of the internal spaces of the pressing cuff 71 and the sensing cuff 73, respectively.

The power supply unit 18 may be a secondary battery such as a lithium ion battery. The power supply unit 18 is electrically coupled to the control substrate 20. The power supply unit 18 supplies power to the control substrate 20.

As illustrated in FIGS. 4 and 6, the control substrate 20 may include a substrate 51, an acceleration sensor 52, a communication unit 53, a storage 54, and a controller 55. The control substrate 20 is constituted by mounting the acceleration sensor 52, communication unit 53, storage 54 and controller 55 on the substrate 51.

The substrate 51 is fixed to the base 33 of the casing 11 with screws or the like.

The acceleration sensor 52 may be a triaxial acceleration sensor. The acceleration sensor 52 outputs to the controller 55 an acceleration signal indicating the acceleration of the main body 3 in three directions orthogonal to each other. The acceleration sensor 52 may be used for the measurement of the amount of activity of the living body wearing the blood pressure measurement device 1, based on the detected acceleration.

The communication unit 53 is configured to transmit information to, and receive information from, an external device in a wireless or wired manner. The communication unit 53 may transmit the information controlled by the controller 55 and information such as the measured blood pressure values and pulse rate to the external device via a network, receive software update programs and the like from the external device via the network and send the programs to the controller.

In the present embodiment, the network may be, but is not limited to, the Internet. The network may be a local area network (LAN) provided in a hospital, or may be a form of direct communication with an external device through a cable provided with a terminal of a specific standard such as a USB. For this reason, the communication unit 53 may have multiple components including a wireless antenna and a micro USB connector.

The storage 54 stores program data for controlling the entire blood pressure measurement device 1 and the fluid circuit 7, setting data for the setting of various functions of the blood pressure measurement device 1, calculation data for calculating blood pressure values and pulse rate from the pressures measured by the pressure sensor 17, and the like in advance. The storage 54 also stores information including the measured blood pressure values and pulse rates.

The controller 55 is constituted by a single CPU or multiple CPUs, and controls the operation of the entire blood pressure measurement device 1 and the operation of the fluid circuit 7. The controller 55 is electrically coupled to the display 12, the operation unit 13, the pump 14, each of the on-off valves 16 and each of the pressure sensors 17, supplying power thereto.

The controller 55 further controls the operations of the display 12, the pump 14 and the on-off valves 16 based on the electric signals output by the operation unit 13 and the pressure sensors 17.

As illustrated in FIG. 4, the controller 55 may include a main CPU 56 configured to control the operation of the entire blood pressure measurement device 1 and a sub-CPU 57 configured to control the operation of the fluid circuit 7. When an instruction for the measurement of a blood pressure is input from the operation unit 13, the sub-CPU 57 may drive the pump 14 and on-off valve 16 to send the compressed air to the pressing cuff 71 and sensing cuff 73.

Furthermore, the sub-CPU 57 controls the driving and stopping of the pump 14, and opening and closing of the on-off valve 16, based on electric signals output by the pressure sensor 17 to selectively send the compressed air to the pressing cuff 71 and sensing cuff 73 and selectively depressurize the pressing cuff 71 and sensing cuff 73. From an electric signal output from the pressure sensor 17, the main CPU 56 obtains measurement results such as blood pressure values, including a systolic blood pressure and diastolic blood pressure as well as a heart rate, and outputs to the display 12 an image signal corresponding to the measurement result.

As illustrated in FIGS. 1 to 3, the strap 4 includes a first strap 61 attached to one pair of lugs 31a and a spring rod 31b, and a second strap 62 attached to the other pair of lugs 31a and the other spring rod 31b.

The first strap 61, referred to as a "main end", is shaped into a rectangle. The first strap 61 includes a first hole 61a provided in one end of the first strap 61 and extending orthogonally to the longitudinal direction of the first strap 61, a second hole 61b provided in the other end and extending orthogonally to the longitudinal direction of the first strap 61, and a buckle 61c attached to the second hole 61b. The first hole 61a has an inner diameter sufficient for the spring rod 31b to be inserted, and for the first strap 61 to rotate around the spring rod 31b. In other words, the first strap 61 is arranged between a pair of lugs 31a with the spring rod 31b inserted into the first hole 61a, thereby being rotatably supported by the outer casing 31.

The second hole 61b is provided at the tip of the first strap 61.

The buckle 61c includes a rectangular frame-shaped body 61d and a prodding stick 61e rotatably attached to the frame-shaped body 61d. One side of the frame-shaped body 61d having the prodding stick 61e is inserted into the second hole 61b, and the frame-shaped body 61d is rotatably attached to the first strap 61.

The second strap 62, referred to as a "blade end", is shaped into a rectangle having a suitable width to be inserted through the frame-shaped body 61d. The second strap 62 further includes small holes 62a through which the prodding stick 61e is inserted. The second strap 62 has a third hole 62b provided in one end and extending orthogonally to the longitudinal direction of the second strap 62. The third hole 62b is configured in a manner such that the spring rod 31b can be inserted, and has an inner diameter sufficient for the second strap 62 to rotate around the spring rod 31b. In other words, the second strap 62, which is arranged between a pair of lugs 31a with the spring rod 31b arranged in the third hole 62b, is rotatably supported by the outer casing 31.

With the second strap 62 inserted through the frame-shaped body 61d and the prodding stick 61e inserted through a small hole 62a, the first strap 61 and second strap 62 are integrally connected, making the strap 4 together with the outer casing 31 into a loop to conform to the wrist 100 in the circumferential direction.

The curler 5 is formed of a resin material into a band that is bent along the circumferential direction of the wrist.

The curler 5 may have one end fixed between the base 33/flow passage cover 34 and the back cover 35 of the main body 3 and the other end in the vicinity of the main body 3. As illustrated in FIG. 5, the curler 5 may be fixed to the outer surface of the back cover 35, with one end protruding from the back cover 35 on the side of one pair of lugs 31a; and the curler 5 may protrude from the other pair of lugs 31a of the back cover 35, and extend from one end toward the other end so that the other end can be brought to a position adjacent to the one end.

A specific example is illustrated in FIGS. 1 to 3 and 12: the curler 5 may be bent along the circumferential direction of the wrist 100 when viewed in a direction perpendicular to the circumferential direction of the wrist 100, or in other words, in the side view from the longitudinal direction of the wrist 100. The curler 5 may extend from the main body 3 to the back of the wrist 100 and one lateral side of the wrist 100, to the palm side of the wrist 100, and to the other lateral side of the wrist 100. That is, the curler 5 bending along the circumferential direction of the wrist 100 surrounds most of the circumferential direction of the wrist 100, with the two ends separated while keeping a certain distance from each other.

The rigidity of the curler 5 has flexibility and shape retention. The flexibility represents deformation in the direction of the diameter of the curler 5 when an external force is applied to the curler 5. For instance, when pressed by the strap 4, the curler 5 is deformed, when viewed from the side, to become closer to the wrist, to extend along the shape of the wrist, or to conform to the shape of the wrist. The shape retention represents the capability of maintaining the original shape of the curler 5 when no external force is applied. In the present embodiment, the curler 5 maintains its curved shape along the circumferential direction of the wrist.

The curler 5 may be prepared with polypropylene to have a thickness of approximately 1 millimeter. The curler 5 supports the cuff structure 6 along the inner surface of the curler 5.

As illustrated in FIGS. 1 to 5 and 10 to 12, the cuff structure 6 includes a pressing cuff 71, a back plate 72, and a sensing cuff 73. The pressing cuff 71, back plate 72 and sensing cuff 73 are stacked and integrally formed in the cuff structure 6. The cuff structure 6 is fixed to the inner surface of the curler 5.

The pressing cuff 71 shows an exemplary cuff. The pressing cuff 71 is fluidically coupled to the pump 14 by way of the flow passage unit 15. The pressing cuff 71 is inflated to pressurize the back plate 72 and sensing cuff 73 toward the living body side. The pressing cuff 71 includes a plurality of air bags 81, a tube 82 communicating with the air bags 81, a connector 83 attached to the tip of the tube 82, and first guides 84 in the air bags 81.

An air bag 81 has a bag-like structure. In the present embodiment, the blood pressure measurement device 1 is configured to send air with the pump 14, and air bags are therefore employed. If any fluid other than air is adopted, the bag-like structure may be a fluid bag for liquid or the like.

A plurality of air bags 81 are stacked together and fluidically communicate with each other in the stacking direction. Specifically, the pressing cuff 71 may include two air bags 81 fluidically communicating with each other in the stacking direction, a tube 82 at one end of one of the air bags 81 in the longitudinal direction, the connector 83 at the tip of the tube 82, and the first guides 84 on the main surface of one of the two air bags 81.

In the pressing cuff 71, the main surface of the one air bag 81 is fixed to the inner surface of the curler 5. The pressing cuff 71 may be adhered to the inner surface of the curler 5 with double-sided tape or adhesive.

Each of the two air bags 81 are formed into a rectangle elongated in one direction. An air bag 81 may be formed by combining two sheet members 86 elongated in one direction to weld the edges thereof. Specifically, the two air bags 81 may include a first sheet member 86*a*, a second sheet member 86*b* forming the first air bag 81 together with the first sheet member 86*a*, a third sheet member 86*c* adhered integrally to the second sheet member 86*b*, a fourth sheet member 86*d* forming the second air bag 81 together with the third sheet member 86*c*, stacked in this order from the living body side, as shown in FIGS. 9 to 11.

The first sheet member 86*a* has a plurality of first guides 84 on its outer surface on the living body side. The first sheet member 86*a* and second sheet member 86*b* form an air bag 81 with their four peripheral sides welded. The second sheet member 86*b* and third sheet member 86*c* are arranged to face each other, and include openings 86*b*1 and 86*c*1, respectively, so that the two air bags 81 can fluidically communicate with each other. An adhesive layer or double-sided tape is provided on the outer surface of the fourth sheet member 86*d* on the curler 5 side, and the fourth sheet member 86*d* is adhered to the curler 5 with this adhesive layer or double-sided tape.

The third sheet member 86*c* and fourth sheet member 86*d* form an air bag 81 with their four peripheral sides welded. Furthermore, the tube 82 may be arranged on one side of the third sheet member 86*c* and fourth sheet member 86*d*, and welded and fixed in such a manner as to fluidically communicate with the internal space of the air bag 81. For instance, the third sheet member 86*c* and fourth sheet member 86*d* form the air bag 81 by welding their four peripheral sides with the tube 82 provided between the third sheet member 86*c* and fourth sheet member 86*d*, thereby integrally adhering the tube 82 thereto.

The first guides 84 may be arranged on the outer surface of the stacked air bag 81 on the living body side. When the pressing cuff 71 is inflated to pressurize the living body, the first guides 84 create wrinkles on the main surface of the living body-side air bag 81 of the pressing cuff 71, or in other words in the first sheet member 86*a*, in a direction intersecting the winding direction of the pressing cuff 71 wound around the wrist 100.

The direction intersecting the winding direction represents a direction perpendicular or oblique with respect to the longitudinal direction of the pressing cuff 71. In order to avoid crossing of wrinkles, it is preferable that the first guides 84 create wrinkles that run perpendicular to the winding direction on the living body-side main surface of the living body-side air bag 81, closer to the pressing cuff 71, when inflating the pressing cuff 71 and pressurizing the wrist.

The first guides 84 are arranged on the outer surface of the first sheet member 86*a* of the living body-side air bag 81 of the pressing cuff 71. In other words, the first guides 84 are provided on the outer surface 86*a*1 of the first sheet member 86*a* that forms, of the two air bags 81, the air bag 81 on the wrist 100 side.

The first guides 84 are formed integrally with the first sheet member 86*a*. The first guides 84 may be suitably selected and adopted from grooves, creases such as mountain fold and valley fold, and dashed-line grooves, or may be a combination of any of the aforementioned. When the first guides 84 are grooves, the grooves may be formed by making a concave/convex pattern in part of the first sheet member 86*a*. In the case of the first guides 84 being grooves, the grooves may be formed by making indented portions in the outer surface 86*a*1 of the first sheet member 86*a*. Instead of the configuration in which wrinkles are created perpendicular to the winding direction, the first guides 84 may have a configuration in which grooves are inclined with respect to the winding direction or have alternating inclinations as in those of a trapezoid. The width and depth of each first guide 84 may be suitably selected as long as predetermined wrinkles can be created.

The "predetermined wrinkles" are defined as having a depth that would not divide the internal space of the air bag 81 when the pressing cuff 71 is inflated to bend in accordance with the shape of the wrist 100 in the peripheral direction, and as being arranged in a manner such that no overly proximate adjacent wrinkles would produce a partial pressure loss.

The width, depth, shape and configuration of each of the first guides 84, and intervals of adjacent first guides 84 may be suitably set as long as the predetermined wrinkles can be created. The width, depth, shape, structure and interval may be uniformly set, or may differ from each other.

According to the present embodiment, as illustrated in FIG. 9, the first guides 84 are linear grooves provided in the outer surface 86a1 of the air bag 81 and extending in a direction perpendicular to the longitudinal direction of the air bag 81. Furthermore, the first guides 84 are arranged at regular intervals in the outer surface 86a1 of the first sheet member 86a in the living body-side air bags 81 of the pressing cuff 71. The first guides 84 may be arranged at intervals of 15 millimeters.

The tube 82 is coupled to one of the two air bags 81, and is arranged at one end of this air bag 81 in the longitudinal direction. Specifically, the tube 82 may be arranged, of the two air bags 81, in the air bag 81 on the curler 5 side and at the end thereof close to the main body 3. The tube 82 has a connector 83 at its tip end. The tube 82 constitutes, of the fluid circuit 7, the flow passage between the main body 3 and the air bag 81. The connector 83 is coupled to the connected portion 34a of the flow passage cover 34. The connector 83 may be a nipple.

The back plate 72 is adhered to the outer surface 86a1 of the first sheet member 86a of the pressing cuff 71 with an adhesive layer or double-sided tape. The back plate 72 may be formed of a resin material into a plate. The back plate 72 may be formed of polypropylene into a plate approximately 1 millimeter thick. The back plate 72 has a shape-conforming capability.

The shape-conforming capability represents the deformability of the back plate 72 that can conform to the shape of the contact portion of the wrist 100. The contact portion of the wrist 100 represents the portion brought into contact with the back plate 72, and this contact may be direct contact or indirect contact.

In view of this, with the shape-conforming capability, the back plate 72 may be deformed in a manner such that the back plate 72 or the sensing cuff 73 arranged on the back plate 72 conforms to the shape of the wrist 100, or may be deformed to conform to the shape of the wrist 100 until it substantially fits the wrist 100. Here, the back plate 72 may be provided in the pressing cuff 71 or between the pressing cuff 71 and the sensing cuff 73.

The back plate 72 may have a plurality of grooves 72a at facing positions on the two main surfaces of the back plate 72, at regular intervals in the longitudinal direction of the back plate 72. As a result, the back plate 72 is thinner in the portion where the grooves 72a are provided than in the portion where the grooves 72a are not provided, making the portions with the grooves 72a easily deformable. The back plate 72 thereby demonstrates the shape-conforming capability of deforming in accordance with the shape of the wrist 100. The back plate 72 is designed to have a length sufficient to cover the palm side of the wrist 100.

The back plate 72, when being in the state of conforming to the shape of the wrist 100, conveys the pressing force from the pressing cuff 71 to the main surface of the sensing cuff 73 on the back plate 72 side.

The sensing cuff 73 is fixed to the main surface of the back plate 72 on the living body side. The sensing cuff 73 is brought into direct contact with the area of the wrist 100 where the arteries run, as illustrated in FIG. 12. The sensing cuff 73 is formed to have the same shape as the back plate 72 or to be smaller than the back plate 72 in the longitudinal direction and width direction of the back plate 72. The sensing cuff 73 is inflated to pressurize an artery 110 on the palm side of the wrist 100. The sensing cuff 73 is pressurized toward the living body side by the inflated pressing cuff 71 with the back plate 72 interposed between.

Specifically, the sensing cuff 73 may include one air bag 91, a tube 92 communicating with the air bag 91, a connector 93 provided at the tip of the tube 92, and guides 94 provided on one of the main surfaces of the air bag 91. In the sensing cuff 73, one of the main surfaces of the air bag 91 is fixed to the back plate 72. The sensing cuff 73 may be adhered to the living body-side main surface of the back plate 72 with double-sided tape or an adhesive layer.

The air bag 91 has a bag-like structure. In the present embodiment, the blood pressure measurement device 1 is configured to send air with the pump 14, meaning that air bags are therefore employed. If any fluid other than air is adopted, the bag-like structure may be a fluid bag for liquid or the like. A plurality of air bags 91 are stacked together, and fluidically communicate with each other in the stacking direction.

The air bag 91 is formed into a rectangle elongated in one direction. The air bag 91 may be prepared by combining two sheet members elongated in one direction and welding their edges with heat. Specifically, the air bag 91 may include a fifth sheet member 96a and a sixth sheet member 96b arranged in this order from the living body side, as illustrated in FIGS. 9 and 10.

The fifth sheet member 96a includes a plurality of guides 94 on its outer surface on the living body side. For example, a tube 92 may be arranged on one side of the fifth sheet member 96a and the sixth sheet member 96b in such a manner as to fluidically communicate with the internal space of the air bag 91, and the fifth sheet member 96a and sixth sheet member 96b may be welded with the tube 92 fixed. The tube 92 may be integrally welded through the formation of the air bag 91 by welding the four edges of the fifth sheet member 96a and the sixth sheet member 96b with the tube 92 between the fifth sheet member 96a and the sixth sheet member 96b.

The tube 92 is attached to one end of the air bag 91 in the longitudinal direction. Specifically, the tube 92 is attached to the end of the air bag 91 closer to the main body 3. The tube 92 has a connector 93 at its tip. The tube 92 constitutes, of the fluid circuit 7, a flow passage between the main body 3 and the air bag 91. The connector 93 is coupled to the connected portion 34a of the flow passage cover 34. The connector 93 may be a nipple.

The second guides 94 are provided in the outer surface of the air bag 91 on the living body side. When the sensing cuff 73 is inflated to pressurize the living body, the second guides 94 create wrinkles in the main surface of the living body-side air bag 91 of the sensing cuff 73, or in other words in the fifth sheet member 96a, in a direction intersecting the winding direction of the pressing cuff 71 around the wrist 100. The winding direction of the pressing cuff 71 is the same direction as the winding direction of the sensing cuff 73.

The direction intersecting the winding direction represents a direction perpendicular or oblique with respect to the longitudinal direction of the pressing cuff 71 and sensing cuff 73. It is preferable that the second guides 94 create wrinkles that run perpendicular to the winding direction on the living body-side main surface of the air bag 91 when the pressing cuff 71 and sensing cuff 73 are inflated to pressurize the wrist 100.

The second guides 94 are provided in the outer surface 96a1 of the fifth sheet member 96a of the air bag 91 in the sensing cuff 73. The second guides 94 are integrally formed with the fifth sheet member 96a. The second guides 94 may be suitably selected and adopted from grooves, creases such as mountain fold and valley fold, and dashed-line grooves, or may be a combination of any of the aforementioned. When the second guides 94 are grooves, the grooves may be formed by making a concave/convex pattern in part of the fifth sheet member 96a. In the case in which the second guides 94 are grooves, the grooves may be formed by making indented portions in the outer surface 96a1 of the fifth sheet member 96a.

Instead of a configuration in which wrinkles are created perpendicular to the winding direction, the second guides 94 may have a configuration in which grooves are inclined with respect to the winding direction or have alternating inclinations as in those of a trapezoid. The width and depth of each of the second guides 94 may be suitably selected as long as predetermined wrinkles can be created.

The "predetermined wrinkles" are defined as having a depth that would not divide the internal space of the air bag 91 when the sensing cuff 73 is inflated to bend in accordance with the shape of the wrist 100 in the peripheral direction, and as being arranged in a manner such that no overly proximate adjacent wrinkles would produce a partial pressure loss.

The width, depth, shape and configuration of each of the second guides 94, and intervals of adjacent second guides 94 may be suitably set as long as the predetermined wrinkles can be created. The width, depth, shape, structure and interval may be uniformly set, or may differ from each other.

According to the present embodiment, as illustrated in FIG. 9, the second guides 94 are linear grooves provided in the outer surface 96a1 and extending in a direction perpendicular to the longitudinal direction of the air bag 91. Furthermore, the second guides 94 are arranged at regular intervals in the outer surface 96a1 of the fifth sheet member 96a in the living body-side air bags 91 of the sensing cuff 73. The second guides 94 may be arranged at intervals of, for example, 15 millimeters.

It is preferable that the second guides 94 are arranged at the same positions, with respect to the winding direction of the pressing cuff 71, as the first guides 84 in the area of the pressing cuff 71 facing the sensing cuff 73.

The sheet members 86 and 96 that constitute the pressing cuff 71 and sensing cuff 73 are prepared with a thermoplastic elastomer. The thermoplastic elastomer for the sheet members 86 and 96 may be thermoplastic polyurethane (hereinafter, "TPU") resin, polyvinyl chloride resin, ethylene-vinyl acetate resin, thermoplastic polystyrene resin, thermoplastic polyolefin resin, thermoplastic polyester resin or thermoplastic polyamide resin. As the thermoplastic elastomer, the use of TPU is preferable. The sheet material may have a monolayered structure or multi-layered structure.

The sheet members 86 and 96 are not limited to thermoplastic elastomer but may be a thermoset elastomer such as silicone. They may be a combination of a thermoplastic elastomer (such as TPU) and a thermoset elastomer (such as silicone).

When a thermoplastic elastomer is adopted, the sheet members 86b, 86c and 86d that do not include first guides 84 and the sheet member 96b that does not include second guides 94 are shaped with a forming technique such as T-die extrusion, injection, blow molding and calendaring. When a thermoset elastomer is adopted, a forming technique such as mold casting is used.

For a sheet member 86a that includes the first guides 84 and a sheet member 96a that includes the second guides 94, when a thermoplastic elastomer is adopted, a forming technique such as profile extrusion and injection may be used for the formation of a sheet having a concave/convex pattern which serves as grooves or guides 84 in the resin material. Alternatively, a forming technique such as embossing, thermal pressing, vacuum forming or pressure forming may be used for producing a concave/convex pattern which serves as grooves or the guides 84 and 94 in the flat sheet. When a thermoset elastomer is adopted, a forming technique such as mold casting, which uses a mold to which a concave/convex pattern for grooves or the guides 84 and 94 is provided, may be adopted for the sheet member 86a, including the first guides 84 and the sheet member 96a including the second guides 94.

The sheet members 86 and 96 are formed with a forming technique and thereafter sized into a predetermined shape. The sized pieces are bonded through adhesion or welding to form air bags 81 and 91. As a bonding technique, when a thermoplastic elastomer is adopted, high frequency welding or laser welding is used. When a thermoset elastomer is adopted, a molecular adhesive is used.

The fluid circuit 7 is constituted by a casing 11, a pump 14, a flow passage unit 15, on-off valves 16, pressure sensors 17, a pressing cuff 71 and a sensing cuff 73. The on-off valves 16 of the fluid circuit 7 may include two valves, namely a first on-off valve 16A and a second on-off valve 16B, and the pressure sensors 17 may include two sensors, namely a first pressure sensor 17A and a second pressure sensor 17B. An exemplary fluid circuit 7 will be explained below.

As illustrated in FIG. 4, the fluid circuit 7 may include a first flow passage 7a making the pump 14 continuous to the pressing cuff 71, a second flow passage 7b branching from the middle portion of the first flow passage 7a and making the pump 14 continuous to the sensing cuff 73, and a third flow passage 7c connecting the first flow passage 7a with ambient air. The first flow passage 7a includes the first pressure sensor 17A. The first on-off valve 16A is arranged between the first flow passage 7a and the second flow passage 7b. The second flow passage 7b includes the second pressure sensor 17B. The second on-off valve 16B is arranged between the first flow passage 7a and the third flow passage 7c.

In this fluid circuit 7, only the first flow passage 7a is connected to the pump 14 by closing the first on-off valve 16A and the second on-off valve 16B so that the pump 14 and the pressing cuff 71 can be fluidically connected to each other. Furthermore, in the fluid circuit 7, the first flow passage 7a and the second flow passage 7b are connected to each other by opening the first on-off valve 16A and closing the second on-off valve 16B so that the pump 14 and the pressing cuff 71 can be fluidically connected to each other, and the pump 14 and the sensing cuff 73 can also be fluidically connected to each other. In the fluid circuit 7, the first flow passage 7a and the third flow passage 7c are connected to each other by closing the first on-off valve 16A and the second on-off valve 16B so that the pressing cuff 71 can be fluidically connected to ambient air. In the fluid circuit 7, the first flow passage 7a, second flow passage 7b and third flow passage 7c are connected to each other by opening the first on-off valve 16A and the second on-off valve 16B so that the pressing cuff 71 and sensing cuff 73 can be fluidically connected to ambient air.

Figure 14:
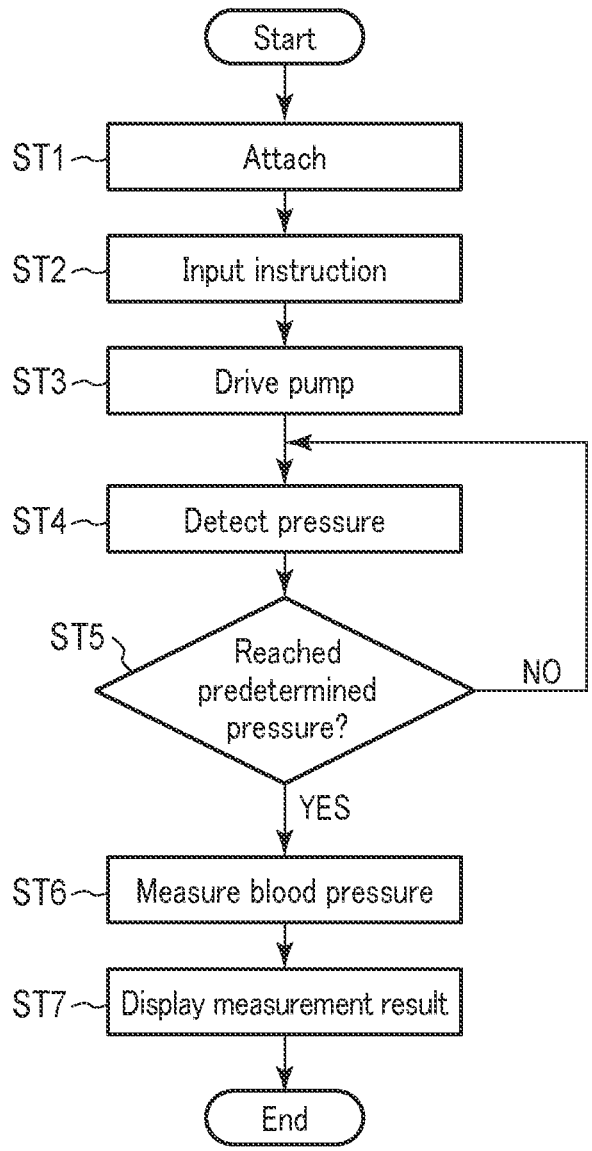
FIG. 14 is a flowchart showing an exemplary use of the blood pressure measurement device.
Figure 15:
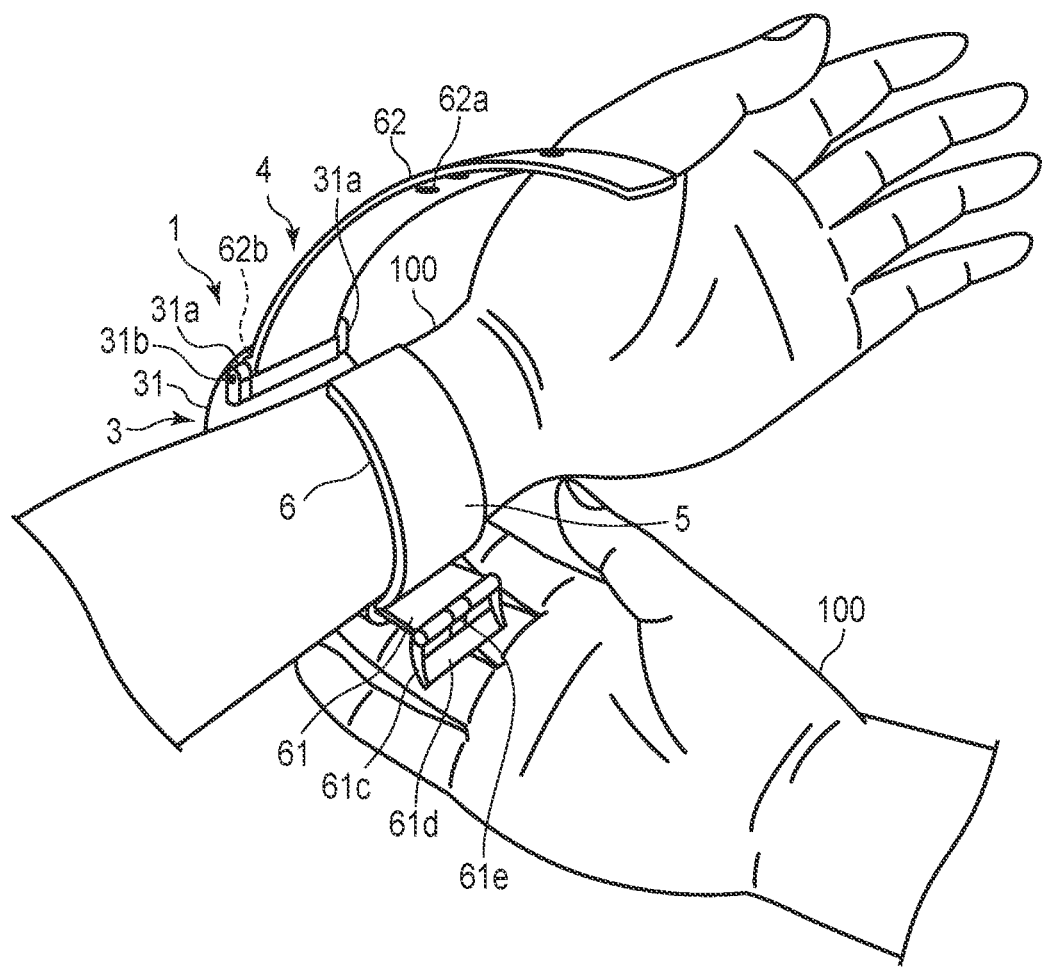
FIG. 15 is a perspective view of the blood pressure measurement device when being attached around the wrist.

Next, an exemplary measurement of a blood pressure value using the blood pressure measurement device 1 will be explained with reference to FIGS. 14 to 17. FIG. 14 is a flowchart of the exemplary blood pressure measurement with the blood pressure measurement device 1, which includes both the user's operation and the operation of the controller 55. FIGS. 15 to 17 show an example of the user wearing the blood pressure measurement device 1 around the wrist 100.

First, the user attaches the blood pressure measurement device 1 around the wrist 100 (step ST1). Specifically, the user may place the wrist 100 into the curler 5, as illustrated in FIG. 15.

At this stage, the main body 3 and sensing cuff 73 of the blood pressure measurement device 1 are placed at positions of the curler 5 that face each other, and therefore the sensing cuff 73 can be placed on the palm side of the wrist 100 where the artery 110 runs. This means that the main body 3 is placed on the back side of the wrist 100. Thereafter, the user threads the second strap 62 through the frame-shaped body 61d of the buckle 61c of the first strap 61 with the hand to which the blood pressure measurement device 1 is not attached, as illustrated in FIG. 16. Then, the user pulls the second strap 62 to tighten the part provided on the inner surface of the curler 5, or in other words the cuff structure 6, onto the wrist 100, and threads the prodding stick 61e into a small hole 62a. In this manner, as illustrated in FIG. 17, the first strap 61 and second strap 62 are connected to each other, and the blood pressure measurement device 1 is attached around the wrist 100.

Next, the user manipulates the operation unit 13 to input an instruction corresponding to the initiation of the blood pressure measurement. The operation unit 13, on which the instruction input manipulation is performed, outputs an electric signal corresponding to the initiation of the measurement to the controller 55 (step ST2). Upon the receipt of this electric signal, the controller 55 may open the first on-off valve 16A and close the second on-off valve 16B, and drive the pump 14 to supply compressed air to the pressing cuff 71 and sensing cuff 73 through the first flow passage 7a and second flow passage 7b (step ST3). This initiates the inflation of the pressing cuff 71 and sensing cuff 73.

The first pressure sensor 17A and second pressure sensor 17B detect the pressures of the pressing cuff 71 and sensing cuff 73, respectively, and outputs electric signals corresponding to these pressures to the controller 55 (step ST4). Based on the received electric signals, the controller 55 determines whether or not the pressures of the internal spaces of the pressing cuff 71 and sensing cuff 73 have reached the predetermined pressures for the blood pressure measurement (step ST5). For instance, if the internal pressure of the pressing cuff 71 has not reached its predetermined pressure while the internal pressure of the sensing cuff 73 has reached its predetermined pressure, the controller 55 closes the first on-off valve 16A to supply the compressed air through the first flow passage 7a.

When the internal pressure of the pressing cuff 71 and the internal pressure of the sensing cuff 73 both reach their corresponding predetermined pressures, the controller 55 stops driving the pump 14 ("yes" at step ST5). In this case, the pressing cuff 71 has been sufficiently inflated as illustrated in FIG. 12, and the inflated pressing cuff 71 thereby pressurizes the wrist 100 and the back plate 72. Furthermore, the pressing cuff 71 has wrinkles created along the first guides 84.

The sensing cuff 73 is inflated with a predetermined amount of air supplied in order to bring its internal pressure to a pressure level required for the measurement of the blood pressure. The sensing cuff 73 is thereby pressed toward the wrist 100 by the back plate 72 that is pressed by the pressing cuff 71. The sensing cuff 73 creates wrinkles along the second guides 94. As a result, the sensing cuff 73 pressurizes the artery 110 in the wrist 100 and blocks the artery 110, as illustrated in FIG. 13.

Furthermore, the controller 55 controls the second on-off valve 16B to increase the pressure of the internal space of the pressing cuff 71 by repeating the opening and closing of the second on-off valve 16B or adjusting the degree of opening of the second on-off valve 16B. Based on the electric signal output by the second pressure sensor 17B in this process, the controller 55 acquires the results of the measurement such as blood pressure values including the systolic and diastolic blood pressures, and heart rate.

In the above explained example, the timings of opening and closing the first on-off valve 16A and the second on-off valve 16B at the time of blood pressure measurement can be suitably set, and the controller 55 calculates the blood pressure during the process of pressurizing the pressing cuff 71. The blood pressure, however, may be calculated during the process of depressurizing the pressing cuff 71 or during both the processes of pressurizing and depressurizing the pressing cuff 71. Thereafter, the controller 55 outputs an image signal corresponding to the acquired measurement result to the display 12.

Upon receipt of the image signal, the display 12 displays the measurement result on the screen. The user views the display 12 and thereby ascertains the measurement result. When the measurement is completed, the user removes the prodding stick 61e from the small holes 62a, removes the second strap 62 from the frame-shaped body 61d, and pulls the wrist 100 from the curler 5, thereby removing the blood pressure measurement device 1 from the wrist 100.

In the blood pressure measurement device 1 having the above structure according to the first embodiment, first guides 84 and second guides 94 are provided for creating wrinkles in the outer surface of the pressing cuff 71 and the outer surface of the sensing cuff 73 of the cuff structure 6, respectively, on the living body side. With such a configuration, when the pressing cuff 71 and the sensing cuff 73 of the cuff structure 6 on the inner surface of the curler 5 are inflated, wrinkles can be created at predetermined positions of the pressing cuff 71 and the sensing cuff 73 on the living body side. In this manner, the accuracy of the measurement result of the measured blood pressure can be improved in the blood pressure measurement device 1.

This effect is explained in detail below. The curler 5 of the blood pressure measurement device 1 is shaped to extend along the circumferential direction of the wrist 100, and therefore the pressing cuff 71 and the sensing cuff 73 are shaped to bend with a predetermined curvature. When the pressing cuff 71 is inflated, a difference appears in the curvature radius between the inner peripheral surface and the outer peripheral surface. This creates a difference in the peripheral length of the inflated pressing cuff 71 between the inner peripheral surface and the outer peripheral surface, which is an inner/outer peripheral difference. In a similar manner, when the sensing cuff 73 is inflated, the difference in the curvature radius between the inner peripheral surface side and the outer peripheral surface creates a difference in the peripheral length of the inflated sensing cuff 73 between the inner peripheral surface and the outer peripheral surface, which is an inner/outer peripheral difference.

With this inner/outer peripheral difference, the inner peripheral surfaces of the pressing cuff 71 and the sensing cuff 73 are bent at some portions, creating wrinkles toward the outer peripheral surface in the radial direction. The created wrinkles tend to have a larger depth at portions with a smaller curvature radius.

The wrinkles may cause, depending on their positions and depths, division of the internal space of the pressing cuff 71 and sensing cuff 73 or a loss in the inflating pressure. In other words, the wrinkles created in the inner peripheral surface of the pressing cuff 71 and sensing cuff 73 may become a factor behind adverse effects on the measurement result of the blood pressure, such as reduction in the accuracy of the blood pressure measurement and variation in measurement results.

In the blood pressure measurement device 1 according to the present embodiment, the main body 3 and the sensing cuff 73 are arranged at the positions facing each other across the curler 5. For this reason, if a deep wrinkle is created in the middle portion of the pressing cuff 71 stretching from the main body 3 to the sensing cuff 73, this wrinkle may divide the internal space of the pressing cuff 71 or cause a pressure loss. If this is the case, the pressure inside the region of the pressing cuff 71 that pressurizes the sensing cuff 73 would not increase to reach the predetermined pressure, preventing an accurate value from being acquired as the blood pressure measurement result.

Furthermore, the controller 55 detects the vibration (pulse wave) of the artery wall, and detects the blood pressures by determining the pressure of the sensing cuff 73 when the pulse wave surges, as a systolic blood pressure, and determining the pressure when no change occurs, as a diastolic blood pressure. However, if the internal space of the sensing cuff 73 is divided, or if a loss of pressure occurs, the detection of the vibration of the artery wall or of the systolic blood pressure and diastolic blood pressure may not be accurately conducted.

As described above, the guides 84 and 94 are provided in the pressing cuff 71 and the sensing cuff 73, according to the present embodiment, to serve as starting points of wrinkling when the pressing cuff 71 and sensing cuff 73 are inflated and an inner/outer peripheral difference appears between their inner peripheral surfaces and outer peripheral surfaces. Thus, the wrinkles can be formed in the pressing cuff 71 and sensing cuff 73 from the guides 84 and 94 as the starting points. By providing a predetermined number of guides 84 and 94, the positions and depths of wrinkles, which are generally caused by the inner/outer peripheral difference, can be controlled. Furthermore, even when the conditions of use of the blood pressure measurement device 1 vary, or when the thickness of the wrist 100 varies depending on the user, the numbers and depths of wrinkles are still controllable with the arrangement of the guides 84. Thus, variations in the blood pressure measurement results can be avoided at the blood pressure measurement, and the accuracy of the blood pressure measurement result can be improved.

Furthermore, the second guides 94 in the sensing cuff 73 are arranged to face the first guides 84 in the area facing the sensing cuff 73, with the back plate 72 of the pressing cuff 71 interposed between. Thus, when the pressing cuff 71 presses the sensing cuff 73, the area of the pressing cuff 71 in which wrinkles are not created presses the area of the sensing cuff 73 in which wrinkles are not created. As a result, the pressing force of the pressing cuff 71 is effectively conveyed to the surface of the sensing cuff 73 being in contact with the wrist 100. The sensing cuff 73 can thereby effectively pressurize the area in which the artery runs, improving the accuracy of the blood pressure measurement.

In addition, the guides 84 and 94 are provided by grooves formed in the outer surfaces 86a1 and 96a1 of the sheet member 86a and 96a in accordance with the concave/convex pattern in the pressing cuff 71 and sensing cuff 73, which are guides 84 and 94. In this manner, the pressing cuff 71 and sensing cuff 73 can be formed to have a uniform thickness, without increasing or decreasing the thicknesses of the sheet members 86a and 96a. In addition, the control of wrinkles can be achieved with a simple configuration. Furthermore, the guides 84 and 94 can be formed in the first sheet member 86a that constitutes the pressing cuff 71 and the fifth sheet member 96a that constitutes the sensing cuff 73, at the time of forming the sheet members 86a and 96a or forming the pressing cuff 71 or sensing cuff 73. This facilitates the manufacturing of the cuff structure 6.

As discussed above, in the blood pressure measurement device 1 according to the present embodiment, the guides 84 and 94 that form wrinkles are provided in the living body-side main surfaces of the pressing cuff 71 and sensing cuff 73. The accuracy of the blood pressure measurement result can be thereby improved.

In the present embodiment, the main body 3 is arranged on the back side of the wrist 100; however, the main body 3 may be arranged on the palm side of the wrist 100. That is, the main body 3 may be fixed to the outer surface of the curler 5 where the sensing cuff 73 is arranged. In such a configuration, with the main body 3 arranged on the palm side, the blood pressure measurement device 1 can be arranged in the area where the artery of the wrist 100 runs. This reduces the distance to the sensing cuff 73, which shortens the length of the tube 92 attached to the sensing cuff 73.

Second Embodiment

Next, the pressing cuff 71 according to a second embodiment will be explained with reference to FIGS. 18 and 19.

The second embodiment differs from the blood pressure measurement device 1 of the first embodiment in the cuff structure, and the explanation of the configuration other than the cuff structure is omitted. The same reference numerals are assigned to the same components in the present embodiment as those of the above blood pressure measurement device 1 of the first embodiment, and the detailed explanation is omitted.

Figure 18:
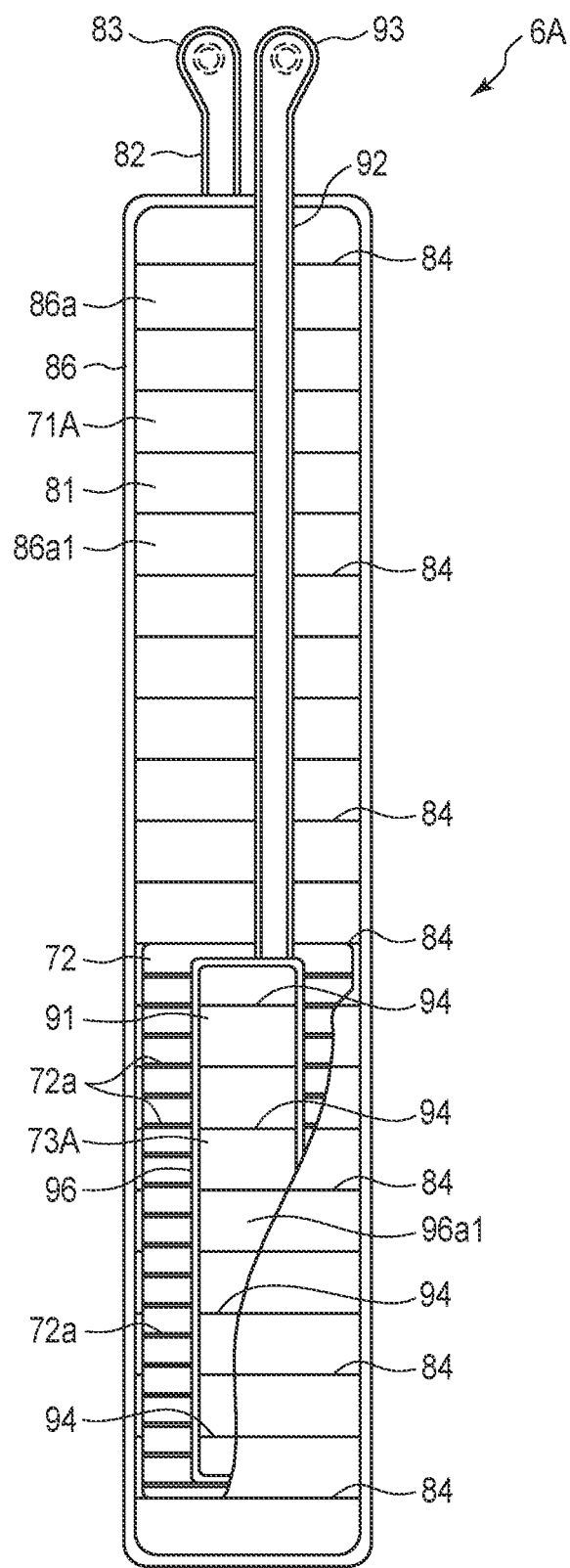
FIG. 18 is a plan view showing the configuration of a cuff structure according to the second embodiment of the present invention.

FIG. 18 is a plan view showing the configuration of a cuff structure 6A according to the second embodiment of the present invention. FIG. 19 is a side view schematically showing the configuration of the blood pressure measurement device 1 using the cuff structure 6A and also schematically showing the configuration of the pressing cuff 71A and sensing cuff 73A when inflated.

As illustrated in FIG. 18, the cuff structure 6A includes a pressing cuff 71A, a back plate 72, and a sensing cuff 73A. In the pressing cuff 71A and sensing cuff 73A, the first guides 84 and second guides 94 are arranged at regular intervals of 5 millimeters. That is, the cuff structure 6A differs from the aforementioned cuff structure 6 of the first embodiment, in the intervals of the first guides 84A and second guides 94A.

Figure 19:
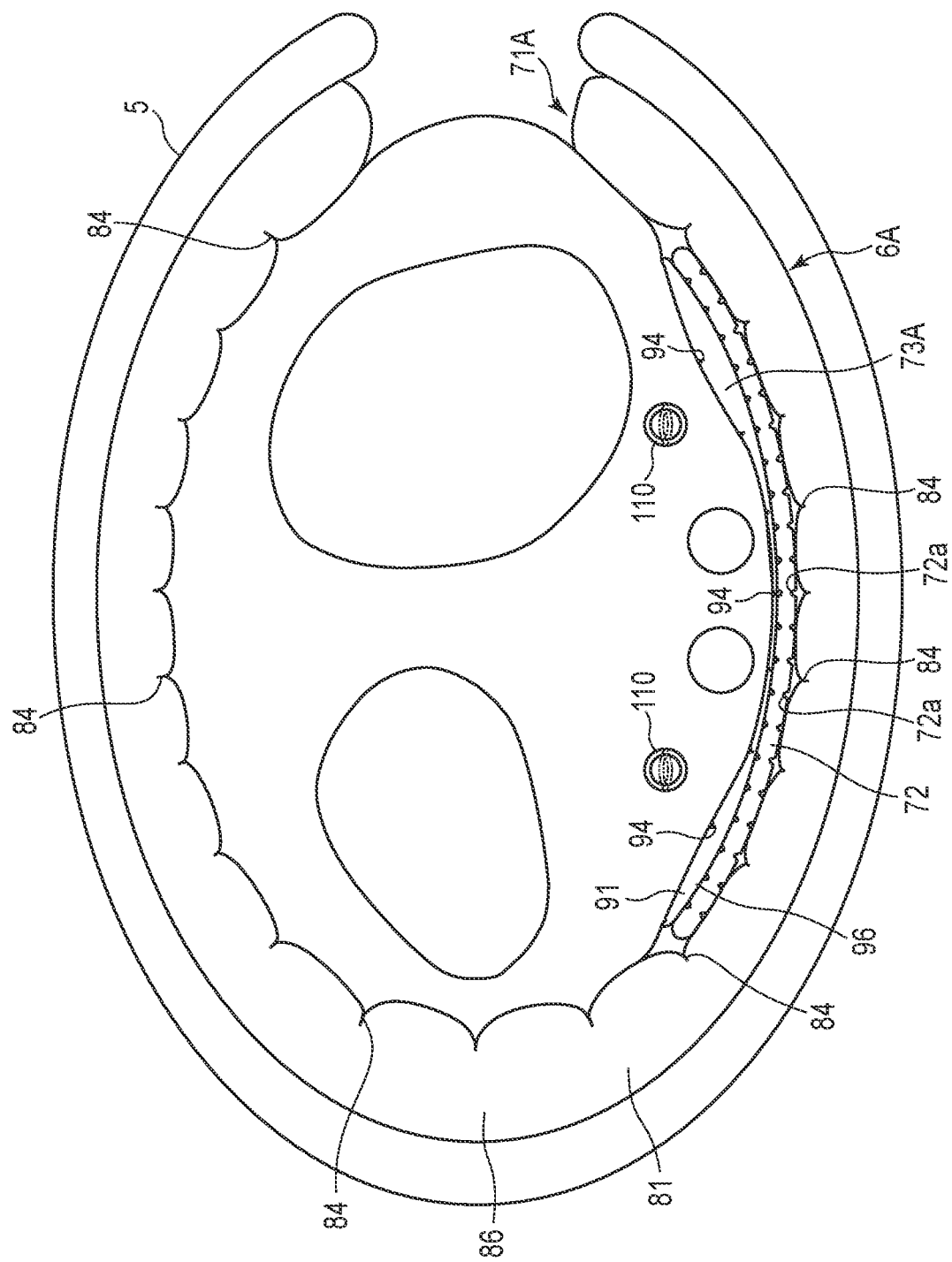
FIG. 19 is a side view schematically showing the configuration of the pressing cuff of the cuff structure when inflated.

In such a cuff structure 6A when inflated, wrinkles are formed at regular intervals as illustrated in FIG. 19, and therefore the depths of the wrinkles become approximately uniform. Furthermore, in the cuff structure 6A, the intervals of the guides 84 and 94 are shorter than those in the cuff structure 6, and the numbers of the guides 84 and 94 are larger than those in the cuff structure 6. Thus, more wrinkles can be formed in the guides 84 and 94 than in the aforementioned cuff structure 6.

With more guides 84 and 94 arranged, the depths of the wrinkles in the pressing cuff 71A can be reduced. The sum of the depths of the wrinkles, which are formed due to the inner/outer peripheral difference, is kept approximately constant. This means that with more wrinkles, the depths of individual wrinkles become smaller. Thus, the internal spaces of the pressing cuff 71A and sensing cuff 73A can be prevented from partially cleaving in the cuff structure 6A, and the inflating pressure would not be lost. As a result, the pressing cuff 71A can pressurize the back plate 72 approximately in the uniform manner, and the sensing cuff 73A can pressurize the wrist 100 approximately in the uniform manner. Thus, the cuff structure 6A improves the accuracy of the result of the blood pressure measurement, in the same manner as the cuff structure 6.

Third Embodiment

Next, the pressing cuff 71 according to the third embodiment will be explained with reference to FIG. 20. The third embodiment differs from the blood pressure measurement device 1 according to the first embodiment in the configuration of the cuff structure, and therefore the configuration other than the cuff structure will be omitted. The same reference numerals are assigned to the same components in the present embodiment as those of the above blood pressure measurement device 1 of the first embodiment, and the detailed explanation is omitted.

Figure 20:
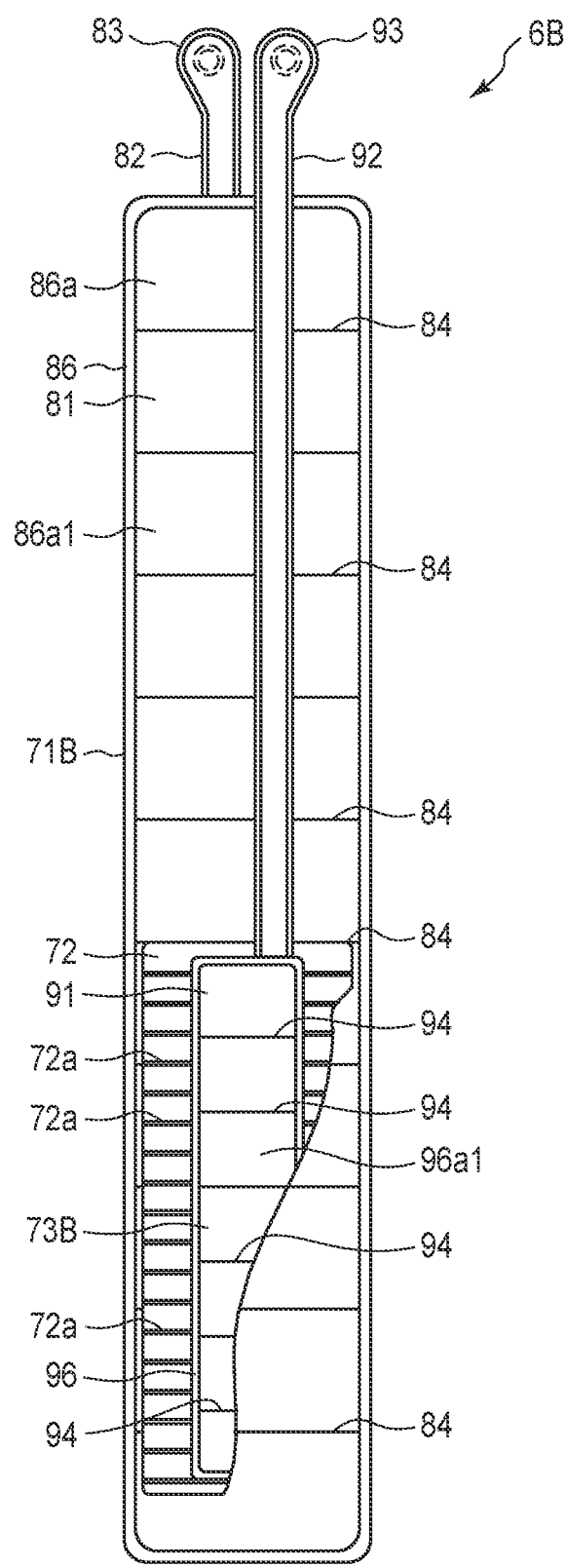
FIG. 20 is a plan view showing the configuration of the cuff structure according to the third embodiment of the present invention.

FIG. 20 is a plan view showing the configuration of the cuff structure 6B according to the third embodiment of the present invention.

As illustrated in FIG. 20, the cuff structure 6B includes a pressing cuff 71B, a back plate 72, and a sensing cuff 73B. The pressing cuff 71B includes first guides 84 at regular intervals. The sensing cuff 73B includes second guides 94 at regular intervals, which differ from the intervals of the first guides 84. The intervals of the second guides 94 may be shorter than the intervals of the first guides 84.

In this manner, the pressing cuff 71B and sensing cuff 73B of the cuff structure 6B form predetermined wrinkles in accordance with the first guides 84 and second guides 94, respectively. Thus, in a manner similar to the cuff structure 6 according to the first and second embodiments, the accuracy of the blood pressure measurement result can be improved.

Furthermore, the cuff structure 6B, which includes the pressing cuff 71B and the sensing cuff 73B having guides 84 and 94 at different sets of regular intervals, can form desirable wrinkles in accordance with the shapes or the like of the pressing cuff 71B and sensing cuff 73B.

In the above configuration, the intervals of the first guides 84 of the pressing cuff 71B are described as being larger than those of the second guides 94 of the sensing cuff 73B, which is not a limitation. The intervals of the first guides 84 may be smaller than the intervals of the second guides 94.

The above embodiments are described merely as examples of the present invention in any aspect. Various improvements and modifications can be made without departing the scope of the invention. A specific structure corresponding to the embodiment may be suitably adopted when the invention is carried out.

REFERENCE SYMBOLS

1 Blood pressure measurement device
1C Blood pressure measurement device
3 Main body
3C Main body
4 Strap
5 Curler
6 Cuff structure
7 Fluid circuit
7*a* First flow passage
7*b* Second flow passage
7*c* Third flow passage
11 Casing
11C Casing
11*a*. Attachment portion
12 Display
13 Operation unit
14 Pump
15 Flow passage unit
16 On-off valve
16A First on-off valve
16B Second on-off valve
17 Pressure sensor
17A First pressure sensor
17B Second pressure sensor
18 Power supply unit
19 Vibration motor
20 Control substrate
31 Outer casing
31*a* Lug
31*b* Spring rod
32 Windshield
33 Base
34 Flow passage cover
34*a* Connected portion
35 Back cover
35*a* Screw
36 Flow passage tube
41 Button
42 Sensor
43 Touch panel
51 Substrate
52 Acceleration sensor
53 Communication unit
54 Storage
55 Controller
61 First strap
61*a* First hole
61*b* Second hole
61*c* Buckle
61*d* Frame-shaped body
61*e* Prodding stick
62 Second strap
62*a* Small hole
71 Pressing cuff
71A Pressing cuff
71B Pressing cuff
71C Pressing cuff
72 Back plate 72a Groove
73 Sensing cuff
81 Air bag
82 Tube
83 Connector
84 First guide
86 Sheet member
86a First sheet member
86a1 Outer surface
86b Second sheet member
86b1 Opening
86c Third sheet member
86c1 Opening
86d Fourth sheet member
91 Bag-like structure
92 Air bag
92 Tube
93 Connector
94 second guide
96 Sheet member
96a Fifth sheet member
96b Sixth sheet member
100 Wrist
110 Artery

The invention claimed is:

1. A blood pressure measurement device comprising:
a pressing cuff that is bag-like and configured to be wound around a measurement target site of a living body and inflated when a fluid is supplied to an internal space of the pressing cuff;
a sensing cuff that is bag-like, on a living body side of the pressing cuff and configured to be inflated when the fluid is supplied to an internal space of the sensing cuff when the pressing cuff is wound around the living body;
a supply device configured to supply the fluid into the pressing cuff and the sensing cuff;
first guides configured to form wrinkles on the living body side of the pressing cuff at positions of the first guides in a direction intersecting a winding direction of the pressing cuff only when the pressing cuff is inflated to pressurize the living body; and
second guides on the living body side of the sensing cuff and configured to form wrinkles on the living body side of the sensing cuff at positions of the second guides in the direction of the winding direction of the pressing cuff only when the sensing cuff is inflated to pressurize the living body, wherein
the first guides are a plurality of grooves on an outer surface of the pressing cuff on the living body side,
the second guides are a plurality of grooves on an outer surface of the sensing cuff on the living body side,
the pressing cuff and the sensing cuff each comprise a plurality of sheet members, and
the first guides and the second guides are on an outer surface of respective ones of the sheet members that are on the living body side.

2. The blood pressure measurement device according to claim 1, wherein
the first guides and the second guides are arranged at regular intervals.

3. The blood pressure measurement device according to claim 1, wherein
the second guides are arranged at same positions with respect to the winding direction of the pressing cuff as the first guides, which are arranged in an area facing to the sensing cuff.

4. The blood pressure measurement device according to claim 1, further comprising:
a back plate arranged on the living body side of the pressing cuff and extending in a circumferential direction of the measurement target site, wherein the sensing cuff is arranged on a living body side of the back plate.

5. The blood pressure measurement device according to claim 1, wherein
the first guides and the second guides form wrinkles in a direction perpendicular to the winding direction of the pressing cuff.

6. The blood pressure measurement device according to claim 1,
wherein the first guides are arranged only on the living body side of the pressing cuff, and
the second guides are arranged only on the living body side of the sensing cuff.

7. The blood pressure measurement device according to claim 1, further comprising a curler,
wherein the pressing cuff is present between the curler and the sensing cuff.

* * * * *